(12) United States Patent
Khaled

(10) Patent No.: US 9,266,937 B2
(45) Date of Patent: Feb. 23, 2016

(54) COMPOSITIONS COMPRISING IL-7 RECEPTOR LIGANDS

(75) Inventor: Annette Khaled, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/992,814

(22) PCT Filed: Dec. 9, 2011

(86) PCT No.: PCT/US2011/064227
§ 371 (c)(1),
(2), (4) Date: Aug. 20, 2013

(87) PCT Pub. No.: WO2012/128806
PCT Pub. Date: Sep. 27, 2012

(65) Prior Publication Data
US 2013/0330296 A1    Dec. 12, 2013

Related U.S. Application Data

(60) Provisional application No. 61/421,980, filed on Dec. 10, 2010.

(51) Int. Cl.
*A61K 38/20* (2006.01)
*C07K 14/54* (2006.01)

(52) U.S. Cl.
CPC ............. *C07K 14/54* (2013.01); *C07K 14/5418* (2013.01)

(58) Field of Classification Search
None
See application file for complete search history.

(56) References Cited

U.S. PATENT DOCUMENTS

| | | | |
|---|---|---|---|
| 7,585,947 B2 | 9/2009 | Morre | 530/351 |
| 7,589,179 B2 * | 9/2009 | Gillies et al. | 530/387.1 |
| 7,708,985 B2 | 5/2010 | Morre | 424/85.2 |
| 8,034,327 B2 | 10/2011 | Morre | 424/85.2 |
| 2005/0054054 A1 | 3/2005 | Foss | 424/85.2 |
| 2007/0122380 A1 | 5/2007 | Goldschneider | 530/530 |
| 2008/0206190 A1 | 8/2008 | Morre | 424/85.2 |

FOREIGN PATENT DOCUMENTS

| | | |
|---|---|---|
| CA | 2820956 | 9/2012 |
| EP | 11861479 | 9/2012 |
| WO | WO 2006/061219 | 6/2006 |
| WO | WO 2012/128806 | 9/2012 |

OTHER PUBLICATIONS

International Search Report issued Apr. 26, 2012 for PCT/US2011/064227 filed Dec. 9, 2011 and published as WO 2012/128860 on Sep. 27, 2012 (Inventor—Annette Khaled // Applicant—University of Central Florida Research Foundation, Inc.) (4 pages).

Written Opinion issued Apr. 26, 2012 for PCT/US2011/064227 filed Dec. 9, 2011 and published as WO 2012/128860 on Sep. 27, 2012 (Inventor—Annette Khaled // Applicant—University of Central Florida Research Foundation, Inc.) (5 pages).

International Preliminary Report on Patentability issued Jun. 12, 2013 for PCT/US2011/064227 filed Dec. 9, 2011 and published as WO 2012/128860 on Sep. 27, 2012 (Inventor—Annette Khaled // Applicant—University of Central Florida Research Foundation, Inc.) (6 pages).

Alpdogan O, et al. (2003). IL-7 enhances peripheral T cell reconstitution after allogeneic hematopoietic stem cell transplantation. J. Clin. Invest 112(7): 1095-1107.

Alpdogan O, et al. (2001). Administration of interleukin-7 after allogeneic bone marrow transplantation improves immune reconstitution without aggravating graft-versus-host disease. Blood 98(7): 2256-2265.

Awong G, et al. (2009). Characterization in vitro and engraftment potential in vivo of human progenitor T cells generated from hematopoietic stem cells. Blood 114(5): 972-982.

Beq S, et al. (2009). Injection of glycosylated recombinant simian IL-7 provokes rapid and massive T-cell homing in rhesus macaques. Blood 114(4): 816-825.

Buzzeo MP, et al. (2007). Hematopoietic stem cell mobilization with G-CSF induces innate inflammation yet suppresses adaptive immune gene expression as revealed by microarray analysis. Exp. Hematol. 35(9): 1456-1465.

Chehtane M, et al. (2010). Interleukin-7 Mediates Glucose Utilization in Lymphocytes through Transcriptional Regulation of the Hexokinase II Gene. Am. J. Physiol Cell Physiol. 298(6):C1560-C1571.

Chung B, et al. (2008). Importance of interleukin-7 in the development of experimental graft-versus-host disease. Biol. Blood Marrow Transplant. 14(1): 16-27.

Chung B, et al. (2007). Prevention of graft-versus-host disease by anti IL-7Ralpha antibody. Blood 110(8), 2803-2810.

de Witte T., et al. (2007). Autologous stem cell transplantation in myelodysplastic syndromes. Semin. Hematol. 44(4): 274-277.

Fry TJ, et al. (2001). A potential role for interleukin-7 in T-cell homeostasis. Blood 97(10): 2983-2990.

Geiselhart LA, et al. (2001) IL-7 administration alters the CD4:CD8 ratio, increases T cell numbers, and increases T cell function in the absence of activation. J Immunol. 166(5): 3019-3027.

Khaled AR, et al. (2005). Cytokine-driven cell cycling is mediated through Cdc25A. J. Cell Biol. 169(5): 755-763.

Kieper WC, et al. (2002). Overexpression of Interleukin (IL)-7 Leads to IL-15-independent Generation of Memory Phenotype CD8(+) T Cells. J Exp Med 195(12): 1533-1539.

Kim K, al. et al (2003). Characterization of an interleukin-7-dependent thymic cell line derived from a p53(-/-) mouse. J. Immunol. Methods 274(1-2): 177-184.

Kittipatarin C, et al. (2007). Interlinking interleukin-7 Cytokine 39(1): 75-83.

Kittipatarin C, et al. (2009). Ex vivo expansion of memory CD8 T cells from lymph nodes or spleen through in vitro culture with interleukin-7 J. Immunol. Methods 344(1): 45-57.

Kittipatarin C, et al. (2010). Cdc25A-Driven Proliferation Regulates Lymphocyte Movement in Response to Interleukin-7 Exp. Hematol. 38(12): 1143-1156.

Kittipatarin C, et al. (2010). The interaction of LCK and the CD4 co-receptor alters the dose response of T-cells to interleukin-7 Immunol. Lett. 131(2): 170-181.

(Continued)

*Primary Examiner* — Dong Jiang
(74) *Attorney, Agent, or Firm* — Akerman LLP

(57) ABSTRACT

Disclosed herein are novel proteins that have reduced binding to the interleukin-7 receptor, compositions containing such proteins, and methods of using the same.

10 Claims, 18 Drawing Sheets

(56) References Cited

OTHER PUBLICATIONS

Kovanen PE, et al. (2004). Cytokines and immunodeficiency diseases: critical roles of the gamma(c)-dependent cytokines interleukins 2, 4, 7, 9, 15, and 21, and their signaling pathways. Immunol. Rev. 202: 67-83.

Link A, et al. (2007). Fibroblastic reticular cells in lymph nodes regulate the homeostasis of naive T cells. Nat. Immunol. 8(11): 1255-1265.

Namen AE, et al. (1988). B cell precursor- growth-promoting activity. Purification and characterization of a growth factor active on lymphocyte precursors. J Exp Med 167(3): 988-1002.

Park JH, et al. (2004). Suppression of IL-7Ralpha transcription by IL-7 and other prosurvival cytokines a novel mechanism for maximizing IL-7-dependent T cell survival. Immunity. 21(2), 289-302.

Rich BE, et al. (1993). Cutaneous lymphoproliferation and lymphomas in interleukin 7 transgenic mice. J Exp Med. 177(2): 305-316.

Sakata T, et al. (1990). Constitutive expression of interleukin-7 mRNA and production of IL-7 by a cloned murine thymic stromal cell line. J. Leukoc. Biol. 48(3): 205-212.

Sawa Y et al. (2009). Hepatic interleukin-7 expression regulates T cell responses. Immunity. 30(3): 447-457.

Schluns KS, et al. (2000) Interleukin-7 mediates the homeostasis of naive and memory CD8 T cells in vivo. Nat Immunol. 1(5), 426-432.

Shalapour S, et al. (2010). Commensal microflora and interferon-gamma promote steady-state interleukin-7 production in vivo. Eur. J. Immunol. 40(9), 2391-2400.

Shultz LD, et al. (2005). Human lymphoid and myeloid cell development in NOD/LtSz-scid IL2R gamma null mice engrafted with mobilized human hemopoietic stem cells. J. Immunol. 174(10) 6477-6489.

Smith KA. (2001). Low-dose daily interleukin-2 immunotherapy: accelerating immune restoration and expanding HIV-specific T-cell immunity without toxicity. AIDS 15 Suppl 2: S28-S35.

Sportes C, et al. (2010). Phase I study of recombinant human interleukin-7 administration in subjects with refractory malignancy. Clin. Cancer Res. 16(2), 727-735.

Sportes C, et al. (2008). Administration of rhIL-7 in humans increases in vivo TCR repertoire diversity by preferential expansion of naive T cell subsets. J. Exp. Med. 205(7) 1701-1714.

Tallman MS. (2007). Treatment of relapsed or refractory acute promyelocytic leukemia. Best. Pract. Res. Clin. Haematol. 20(1), 57-65.

Thiant S, et al. (2010). Plasma levels of IL-7 and IL-15 in the first month after myeloablative BMT are predictive biomarkers of both acute GVHD and relapse. Bone Marrow Transplant. 45(10): 1546-1552.

Vigouroux S, et al. (2007). Long-term outcomes after reduced-intensity conditioning allogeneic stem cell transplantation for low-grade lymphoma: a survey by the French Society of Bone Marrow Graft Transplantation and Cellular Therapy (SFGM-TC). Haematologica. 92(5): 627-634.

von-Freeden-Jeffry U, et al. (1995). Lymphopenia in interleukin (IL)-7 gene-deleted mice identifies IL-7 as a nonredundant cytokine J Exp Med 181(4), 1519-1526.

Warlick ED, et al. (2008). Myeloablative allogeneic bone marrow transplant using T cell depleted allografts followed by post-transplant GM-CSF in high-risk myelodysplastic syndromes. Leuk. Res. 32(9), 1439-1447.

Yamanaka K., et al. (2006). Skin-derived interleukin-7 contributes to the proliferation of lymphocytes in cutaneous T-cell lymphoma. Blood 107(6), 2440-2445.

Kono T, et al. (2008) Characterization and expression analysis of an interleukin-7 homologue in the Japanese pufferfish, *Takifugu rubripes*. The Authors Journal compilation. FEBS Journal. 275:1213-1226.

McElroy C, et al. (2009) Structural and Biophysical Studies of the Human IL-7/IL-7Ra Complex. Structure. 17:54-65.

Communication pursuant to Article 94(3) EPC dated Apr. 28, 2015 for European Application No. 11861479.1 (Inventor—Annette Khaled // Applicant—University of Central Florida Research Foundation, Inc.) (4 pages).

Response to Communication pursuant to Rules 70(2) and 70a(2) EPC dated Feb. 3, 2015 for European Application No. 11861479.1 (Inventor—Annette Khaled // Applicant—University of Central Florida Research Foundation, Inc.) (8 pages).

Communication Noting Loss of Rights pursuant to Rule 112(1) EPC dated Dec. 19, 2014 for European Application No. 11861479.1 (Inventor—Annette Khaled // Applicant—University of Central Florida Research Foundation, Inc.) (1 page).

Response to EPO Form 1224 filed Nov. 12, 20014 for European Application No. 11861479.1 (Inventor—Annette Khaled // Applicant—University of Central Florida Research Foundation, Inc.) (1 page).

Communication Conveying Extended European Search Report dated Apr. 14, 2014 for European Application No. 11861479.1 (Inventor—Annette Khaled // Applicant—University of Central Florida Research Foundation, Inc.) (9 pages).

Response to Communication pursuant to Rules 161(2) and 162 EPC dated Jan. 27, 2014 for European Application No. 11861479.1 (Inventor—Annette Khaled // Applicant—University of Central Florida Research Foundation, Inc.) (4 pages).

Communication pursuant to Rules 161(2) and 162 EPC dated Jul. 17, 2013 for European Application No. 11861479.1 (Inventor—Annette Khaled // Applicant—University of Central Florida Research Foundation, Inc.) (2 pages).

Official Action dated Oct. 3, 2015 for Canadian Application No. 2,820,956 (Inventor—Annette Khaled // Applicant—University of Central Florida Research Foundation, Inc.) (3 pages).

Response to Official Action dated Feb. 2, 2015 for Canadian Application No. 2,820,956 (Inventor—Annette Khaled // Applicant—University of Central Florida Research Foundation, Inc.) (10 pages).

Official Action dated Jan. 8, 2014 for Canadian Application No. 2,820,956 (Inventor—Annette Khaled // Applicant—University of Central Florida Research Foundation, Inc.) (2 pages).

Response to Official Action dated May 27, 2014 for Canadian Application No. 2,820,956 (Inventor—Annette Khaled // Applicant—University of Central Florida Research Foundation, Inc.) (17 pages).

Official Action dated Dec. 18, 2013 for Canadian Application No. 2,820,956 (Inventor—Annette Khaled // Applicant—University of Central Florida Research Foundation, Inc.) (3 pages).

Voluntary Amendment, PCT-PPH Request and Voluntary Submission dated Nov. 22, 2013 for Canadian Application No. 2,820,956 (Inventor—Annette Khaled // Applicant—University of Central Florida Research Foundation, Inc.) (9 pages).

Response to Article 94(3) EPC Communication filed Jul. 24, 2015 for European Application No. 11861479.1 (Inventor—Annette Khaled// Applicant—University of Central Florida Research Foundation, Inc.) (56 pages).

Response to Official Action filed Jul. 8, 2015 for Canadian Application No. 2,820,956 (Inventor—Annette Khaled//Applicant—University of Central Florida Research Foundation, Inc.) (7 pages).

\* cited by examiner

A

B

IL-7AT: GAA TCC ATG GTT TGG TGG CGC CTG TGG TGG CTG TGG TGG CTG CTG CTG CTG CTG CTG CTG TGG CCC ATG GTG TGG GCC
IL-7:                                                                                                    ATG

IL-7AT: TTC CAT GTT TCT TTT AGG TAT ATC TTT GGA CTT CCT CCC CTG ATC CTT GTT CTG TTG CCA GTA GCA
IL-7:   TTC CAT GTT TCT TTT AGG TAT ATC TTT GGA CTT TTT CCT CCC CTG ATC CTT GTT CTG TTG CCA GTA GCA

IL-7AT: TCA TCT GAT TGT GAT ATT GAA GGT AAA GAT GGC AAA CAA TAT GAG AGT GTT CTA ATG GTC AGC ATC
IL-7:   TCA TCT GAT TGT GAT ATT GAA GGT AAA GAT GGC AAA CAA TAT GAG AGT GTT CTA ATG GTC AGC ATC

IL-7AT: GAT CAA TTA TTG GAC AGC ATG AAA GAA ATT GGT GAC AGC ATG AAT TGC CTG

SEQUENCE LISTING

```
<160> NUMBER OF SEQ ID NOS: 10

<210> SEQ ID NO 1
<211> LENGTH: 534
<212> TYPE: DNA
<213> ORGANISM: Homo sapiens

<400> SEQUENCE: 1
atgttccatg tttcttttag gtatatcttt ggacttcctc ccctgatcct tgttctgttg      60
ccagtagcat catctgattg tgatattgaa ggtaaagatg gcaaacaata tgagagtgtt     120
ctaatggtca gcatcgatca attattggac agcatgaaag aaattggtag caattgcctg    180
aataatgaat taactttt taaagacat atctgtgatg ctaataagga aggtatgttt        240
ttattccgtg ctgctcgcaa gttgaggcaa tttcttaaaa tgaatagcac tggtgatttt     300
gatctccact tattaaaagt tcagaaggc acaacaatac tgttgaactg cactggccag     360
```

```
gttaaaggaa gaaaaccagc tgccctgggt gaagcccaac caacaaagag tttggaagaa      420
aataaatctt taaggaaca gaaaaaactg aatgacttgt gtttcctaaa gagactatta      480
caagagataa aaacttgttg gaataaaatt ttgatgggca ctaaagaaca ctga           534
```

<210> SEQ ID NO 2
<211> LENGTH: 177
<212> TYPE: PRT
<213> ORGANISM: Homo sapiens

<400> SEQUENCE: 2

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 3
<211> LENGTH: 540
<212> TYPE: DNA
<213> ORGANISM: Artificial Sequence
<220> FEATURE:
<223> OTHER INFORMATION: Synthetic Construct; Mutated IL-7; Substitution
      at T97 with 3' XhoI Restriction Sequence

<400> SEQUENCE: 3

```
atgttccatg tttcttttag gtatatcttt ggacttcctc ccctgatcct tgttctgttg      60
ccagtagcat catctgattg tgatattgaa ggtaaagatg gcaaacaata tgagagtgtt     120
ctaatggtca gcatcgatca attattggac agcatgaaag aaattggtag caattgcctg     180
aataatgaat ttaacttttt taaaagacat atctgtgatg ctaataagga aggtatgttc     240
ttattccgtg ctgctcgcaa gttgaggcaa tttcttaaaa tgaatagcgt tggtgatttt     300
gatctccact tattaaaagt ttcagaaggc acaacaatac tgttgaactg cactggccag     360
gttaaaggaa gaaaaccagc tgccctgggt gaagcccaac caacaaagag tttggaagaa     420
aataaatctt taaggaaca gaaaaaactg aatgacttgt gtttcctaaa gagactatta     480
caagagataa aaacttgttg gaataaaatt ttgatgggca ctaaagaaca ctgactcgag     540
```

```
<210> SEQ ID NO 4
<211> LENGTH: 177
<212> TYPE: PRT
<213> ORGANISM: Artificial Sequence
<220> FEATURE:
<223> OTHER INFORMATION: Synthetic Construct; Mutated IL-7; Substitution
      at T97 without 3' XhoI Restriction Sequence

<400> SEQUENCE: 4

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Val Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 5
<211> LENGTH: 606
<212> TYPE: DNA
<213> ORGANISM: Artificial Sequence
<220> FEATURE:
<223> OTHER INFORMATION: Synthetic Construct; Mutated IL-7 with HMM
      secretory signal sequence and EcoRI and XhoI Restriction Sites

<400> SEQUENCE: 5
gaatccatgt ggtggcgcct gtggtggctg ctgctgctgc tgctgctgct gtggcccatg      60
gtgtgggcct tccatgtttc ttttaggtat atctttggac ttcctcccct gatccttgtt     120
ctgttgccag tagcatcatc tgattgtgat attgaaggta agatggcaa acaatatgag      180 agtgttctaa tggtcagcat cgatcaatta ttggacagca tgaaagaaat tggtagcaat     240
tgcctgaata atgaatttaa cttttttaaa agacatatct gtgatgctaa taaggaaggt     300
atgtttttat tccgtgctgc tcgcaagttg aggcaatttc ttaaaatgaa tagcgttggt     360
gattttgatc tccacttatt aaaagtttca gaaggcacaa caatactgtt gaactgcact     420
ggccaggtta aggaagaaa accagctgcc ctgggtgaag cccaaccaac aaagagtttg     480
gaagaaaata atctttaaa ggaacagaaa aaactgaatg acttgtgttt cctaaagaga      540
ctattacaag agataaaaac ttgttggaat aaaattttga tgggcactaa agaacactga     600
ctcgag                                                                 606
```

<210> SEQ ID NO 6
<211> LENGTH: 534
<212> TYPE: DNA
<213> ORGANISM: Homo sapiens

<400> SEQUENCE: 6

```
atgttccatg tttctttag gtatatcttt ggacttcctc ccctgatcct tgttctgttg      60
ccagtagcat catctgattg tgatattgaa ggtaaagatg gcaaacaata tgagagtgtt     120
ctaatggtca gcatcgatca attattggac agcatgaaag aaattggtag caattgcctg     180
aataatgaat ttaactttt taaaagacat atctgtgatg ctaataagga aggtatgttt     240
ttattccgtg ctgctcgcaa gttgaggcaa tttcttaaaa tgaatagcac tggtgatttt     300
gatctccact tattaaaagt ttcagaaggc acaacaatac tgttgaactg cactggccag     360
gttaaaggaa gaaaaccagc tgccctgggt gaagcccaac caacaaagag tttggaagaa     420
aataaatctt taaggaaca gaaaaactg aatgacttgt gtttcctaaa agactatta       480
caagagataa aacttgttg gaataaaatt ttgatgggca ctaaagaaca ctga           534
```

<210> SEQ ID NO 7
<211> LENGTH: 177
<212> TYPE: PRT
<213> ORGANISM: Homo sapiens

<400> SEQUENCE: 7

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 8
<211> LENGTH: 152
<212> TYPE: PRT
<213> ORGANISM: Artificial Sequence
<220> FEATURE:
<223> OTHER INFORMATION: Synthetic Construct; Fragment of IL-7A

<400> SEQUENCE: 8

Met Asp Cys Asp Ile Glu Gly Lys Asp Gly Lys Gln Tyr Glu Ser Val

```
1               5                   10                  15
Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
            35                  40                  45

Asp Ala Asn Lys Glu Gly Met Phe Leu Phe Arg Ala Ala Arg Lys Leu
            50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
                100                 105                 110

Ser Leu Glu Glu Asn Lys Ser Leu Lys Glu Gln Lys Lys Leu Asn Asp
            115                 120                 125

Leu Cys Phe Leu Lys Arg Leu Leu Gln Glu Ile Lys Thr Cys Trp Asn
            130                 135                 140

Lys Ile Leu Met Gly Thr Lys Glu
145                 150

<210> SEQ ID NO 9
<211> LENGTH: 63
<212> TYPE: DNA
<213> ORGANISM: Artificial Sequence
<220> FEATURE:
<223> OTHER INFORMATION: Synthetic Construct; Forward primer for mutated
      IL-7

<400> SEQUENCE: 9
atgtggtggc gcctgtggtg gctgctgctg ctgctgctgc tgctgtggcc catggtgtgg    60
gcc                                                                  63

<210> SEQ ID NO 10
<211> LENGTH: 21
<212> TYPE: PRT
<213> ORGANISM: Artificial Sequence
<220> FEATURE:
<223> OTHER INFORMATION: Synthetic Construct; HMM secretory signal
      peptide

<400> SEQUENCE: 10

Met Trp Trp Arg Leu Trp Trp Leu Leu Leu Leu Leu Leu Leu Leu Trp
1               5                   10                  15

Pro Met Val Trp Ala
            20
```

COMPOSITIONS COMPRISING IL-7 RECEPTOR LIGANDS

CROSS-REFERENCE TO RELATED APPLICATIONS

This application is a National Phase Application of International Application No. PCT/US2011/064227 filed Dec. 9, 2011, which claims priority to U.S. Provisional Application 61/421,980 filed on Dec. 10, 2010, each of which is incorporated herein in its entirety by reference.

STATEMENT REGARDING FEDERALLY SPONSORED RESEARCH OR DEVELOPMENT

This invention was made with government support under R01 CA109524 awarded by the National Institutes of Health. The government has certain rights in the invention.

REFERENCE TO SEQUENCE LISTING

The Sequence Listing submitted 11 Jun. 2015 as a text file named "11071_2_Revised_Sequence_Listing.txt", created on 11 Jun. 2015 and having a size of 10,743 bytes, is hereby incorporated by reference pursuant to 37 C.F.R. §1.52(e)(5).

BACKGROUND

Stem cell transplantation (SCT), with adult stem cells, is currently performed to rescue bone marrow cells destroyed by high doses of radiation or chemotherapy used to kill cancer cells. The problem is that many SCTs are unsuccessful, particularly allogeneic SCT in which matched donor stem cells are required. SCT patients can suffer from severe immunodeficiencies due to poor immune reconstitution, leading to infections, relapse of the original cancer or secondary cancers. The development of graft-versus-host disease (GVHD), in which donor lymphocytes attack the recipient's organs, also impedes recovery.

Effective agents to promote post-transplant immune reconstitution and prevent the resurgence of cancer are needed. To this end, cytokines are attractive candidates. The cytokine, Interleukin-7 (IL-7), has potent proliferative capacity. Recent phase 1 clinical trials reported that minimal toxicity was incurred with IL-7 treatment. IL-7, originally described in 1988 as a growth factor for immature B cells (Namen et al., 1988), has emerged as an important regulator of T-cell development (von Freeden-Jeffry et al., 1995) as well as for homeostasis of peripheral T-cells and maintenance of long-term memory T-cells (Schluns et al., 2000; Kieper et al., 2002).

IL-7 is a 25 kDa protein that was discovered as the product of a thymic stromal cell line (Sakata et al., 1990). IL-7 is not produced by lymphocytes and, although IL-7 mRNA has been detected in lymph nodes (Link et al., 2007), the protein itself has not been found in any secondary lymphoid organs. Circulating serum levels of IL-7 in normal individuals are very low (0.3-8.4 pg/mL) (Fry et al., 2001). Originally thought to be constitutively produced, IL-7 production by non-lymphoid cells can be induced upon infection. In response to engagement of Toll-like receptor (TLR) signaling, liver hepatocytes produced IL-7 (Sawa et al., 2009), while the presence of IFN-γ and commensal microflora promoted the production of IL-7 in the intestines (Shalapour et al., 2010). High circulating amounts of IL-7 are not naturally occurring in healthy individuals.

The receptor for IL-7 (IL-7R), expressed by lymphocytes, consists of the IL-7Rα chain and the common cytokine γ chain (γc) (Kovanen and Leonard, 2004). Upon binding of IL-7, the two receptor chains heterodimerize and initiate a series of signaling events mediated through receptor-associated kinases, JAK1/JAK3, which phosphorylate and activate STAT5 (reviewed in (Kittipatarin and Khaled, 2007)). Hence, unlike other cytokines, such as IL-2 or IL-15, where receptor binding affinity regulates activity, it is the amount of IL-7 available to engage the IL-7R that determines the strength of the IL-7 signal transduced. For this reason, over expression of IL-7, as has been achieved with IL-7 transgenic mice, results in severe immune proliferative disorders that cause lymphoma development (Rich et al., 1993; Yamanaka et al., 2006).

What is needed in the art are compositions and methods for increasing growth, survival, and immune response of cells in subjects in need thereof. What is needed are compositions and methods comprising IL-7 that provide beneficial outcomes without severe side effects from increased levels of IL-7.

SUMMARY

The present invention comprises methods and compositions comprising a modified or mutated IL-7 (IL-7A) that modulates the response of the IL-7 receptor (IL-7R). Disclosed herein are compositions comprising IL-7A. Compositions may comprise peptides, polypeptides, antibodies, nucleic acids, vectors, and host cells for making, using, assaying, and evaluating IL-7A.

Methods of the present invention comprise methods for modulating the response of IL-7R, and modulating the immune response of a subject, such as by modulating an immune response or immune system component. Methods may comprise modulating IL-7R function by contacting a cell expressing an IL-7R with an IL-7A protein of the invention. A method of the present invention comprises identifying IL-7A proteins that modulate the activity of IL-7R, and/or an immune component response in a subject. A method of the present invention comprises treating cells to increase growth, survival, and/or immune response by exposing cells to an IL-7A. A method of the present invention comprises treating immunodeficiency in a patient, as well as methods of inducing proliferation of immune cells in a patient. A method of the present invention comprises increasing immune cell reconstitution following stem cell transplantation. A method of the present invention comprises treating stem cells. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several embodiments of the compositions and methods and together with the description, serve to explain the principles of the compositions and methods.

DETAILED DESCRIPTION

Figure 1:
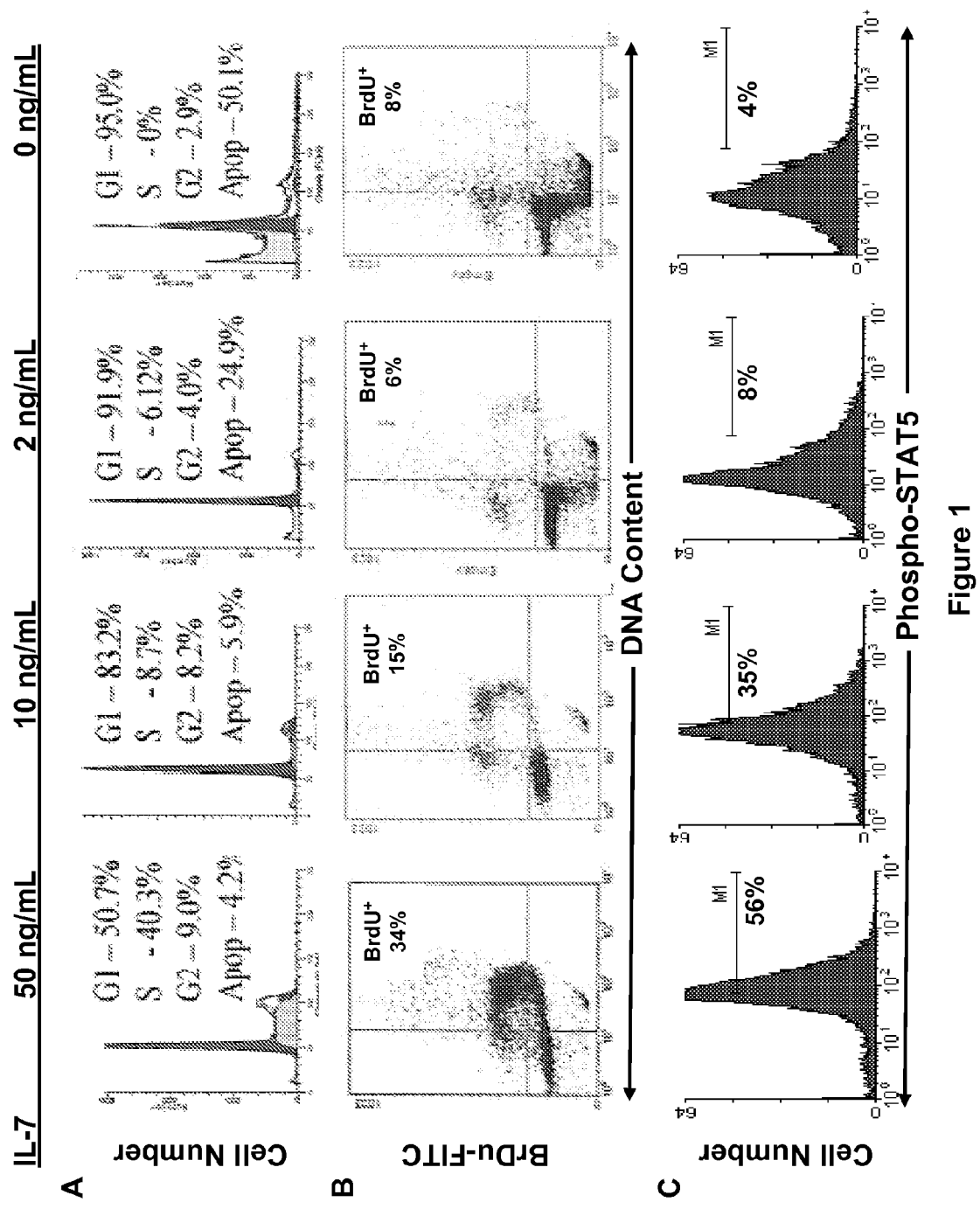
FIG. 1A-C are graphs of survival and proliferation of T-cells.

The present invention comprises methods and compositions comprising IL-7, particularly an attenuated IL-7, referred to herein as IL-7A. Methods of the present invention comprise making IL-7 mutations and mutant proteins (IL-7As), purification of nucleic acid and protein mutants of IL-7, identification of mutant activities and effects on immune system components including but not limited to B cells, T cells, lymphoid tissues and cells, platelets, and components of the hematopoietic system. Methods of the present invention comprise identification and use of mutant IL-7 proteins that function in a modulated manner, either more or less than wild-type IL-7, when compared to native, wild-type IL-7. Methods of the present invention comprise treatment of immune dysfunction, such as immunodeficiency, by administering an effective amount of one or more mutant IL-7 proteins or nucleic acids encoding one or more mutant IL-7 proteins, wherein the one or more includes IL-7 mutant proteins having different mutations. For example, one mutant IL-7 protein has a substitution at $t_{97}$ for valine (IL-7AT). Methods of the present invention comprise administering an IL-7 protein that has one or more mutations, such as substitutions, deletions or insertions. As is understood by those skilled in the art, administering an IL-7 protein means that a quantity, such as microgram to milligram quantities, of a particular protein is administered, and not just one protein molecule. Methods of the present invention comprise modulating the proliferation of immune system components, cells or tissues, such as by inducing, increasing, inhibiting or reducing proliferation of immune components, tissues or cells. Methods of the present invention comprise treating patients or subjects who have undergone, or will undergo, bone marrow transplant. Methods of the present invention comprise modulating immune cell reconstitution following stem cell transplantation. Methods of the present invention comprise treating stem cells, taken from a patient, with an Il-7A protein and then returning those the stem cells into the patient. Methods of the present invention comprise treating stem cells, taken from a subject, with an Il-7A protein and then returning those the stem cells into a different subject. Methods of the present invention comprise administering a composition comprising one or more IL-7A proteins to a subject directly, for example, after a stem cell transplantation has occurred, and for example, during the time of immune reconstitution. Methods of the present invention comprise treating GVHD, for example by reducing the occurrence of GVHD, or reducing the severity of GVHD, or inhibiting GVHD, in subjects who are risk for developing GVHD.

Compositions of the present invention comprise nucleic acid constructs comprising nucleic acids encoding amino acids for attenuated IL-7 proteins (IL-7A). Compositions may comprise nucleic acid that encode, and/or protein fragments of, attenuated IL-7 proteins that, for example, may function in one or more assays in a reduced manner from that of wild-type IL-7. Compositions may comprise nucleic acid constructs that encode, and/or protein fragments of, attenuated IL-7 proteins that, for example, may function in one or more assays in an elevated manner from that of wild-type IL-7. Compositions may comprise nucleic acid constructs that encode, and/or protein fragments of, attenuated IL-7 proteins that, for example, may function in one or more assays in a modulated manner from that of wild-type IL-7. Compositions of the present invention may comprise antibodies, monoclonal or polyclonal, that bind to nucleic acid or proteins disclosed herein. Compositions of the present invention comprise pharmaceutical compositions comprise IL-7 mutants.

As used herein a mutated IL-7, IL-7A or IL-7 mutant, means that one or more nucleic acid bases in a nucleic acid that encodes a polypeptide, and/or amino acids in a polypeptide, have been altered chemically, undergone substitutions with another base or amino acid, and/or deletions or insertions in the sequence have occurred, and such a mutated IL-7 may also be referred to as an attenuated IL-7, or IL-7A. IL-7A or mutated IL-7 may also be referred to as an IL-7 receptor ligand, such as by IL-7AR ligand.

It is known that serum levels of IL-7 in healthy patients are very low, and these levels increase 10 to 100 fold during infection (Sawa et al., 2009). Supraphysiological doses of IL-7, as are used in treatment regimes, cause serum levels of IL-7 to rise 1000-2500 fold over normal (Sportes et al., 2008). A recent study of IL-7 in correlation with the incidence of GVHD in humans revealed that plasma levels of IL-7 were highest 7-14 days post-transplant (median 11.9 pg/ml) and that the incidence of GVHD was associated with the highest plasma levels of IL-7 (Thiant et al., 2010). Hence it remains physiologically possible that high circulating amounts of IL-7 could exacerbate GVHD in SCT patients. Low dosing regimines, while less toxic and more similiar to normal levels of cytokines, are difficult to establish in patients given the short half-lives of cytokines like IL-7.

IL-7, unlike IL-2, is well tolerated, causing T-cell expansion and increased size of lymphoid organs (Sportes et al., 2008; Sportes et al., 2010). In allogeneic transplantation, IL-7 promoted lymphocyte proliferation and had anti-apoptotic effects (Alpdogan et al., 2001; Alpdogan et al., 2003). The present invention is based on the inventors' discovery that high dose native IL-7 treatment to lymphocytes induces proliferation but inhibits lymphocyte movement, which ultimately results in a decrease amount of lymphocytes. The inventors have also found that an attenuated IL-7 signal, resulting from the binding of an IL-7A protein to the IL-7R, results in higher survival signaling and motility of the cells. This in turn results in a higher immune cell yield and a higher rate of survivability upon transplantation in a subject.

According to an embodiment, the invention comprises an IL-7AR ligand, an IL-7A protein, that causes an attenuated signal by the IL-7AR relative to the signal resulting from the native IL-7 molecule. As used herein, the term IL-7AR ligand refers to a variant of IL-7 that is altered from the wild-type IL-7. In a specific embodiment, an IL-7AR ligand having a reduced IL-7R signal refers to an IL-7A protein that has reduced binding function to IL-7R. The mutations may or may not alter the binding site, and may or may not alter binding affinity, but may otherwise interfere with the binding of the IL-7AR ligand to the IL-7R so as to achieve reduced binding which translates into a reduced receptor signal.

The present invention comprises a mutant IL-7. SEQ ID NO. 1 is a nucleotide sequence for wild-type IL-7, as shown below, the nucleotides for Thr at position 97 are underlined. SEQ ID NO. 2 is the amino acid sequence for WT IL-7. SEQ ID NO. 3 is a nucleotide sequence for IL-7AT, wherein the nucleotides at amino acid position 97, Thr (in the WT IL-7) are changed to code for Val, and are underlined. SEQ ID NO. 3 also provides an XhoI restriction site at the 3' end (shown in italics-CTC GAG). SEQ ID NO. 4 is the amino acid sequence encoded by SEQ ID NO. 3 (excluding the 3' XhoI restriction site). SEQ ID NO. 5 is IL-7AT, containing a secretory protein element, HMM (which is underlined) (SEQ ID NO. 10), a 5' EcoRI restriction site (GAATCC), and a 3' XhoI restriction site (CTCGAG). SEQ ID NO. 6 is the nucleic acid sequence for wild-type IL-7, showing amino acid substitution sites to produce an IL-7A. SEQ. ID. NO. 7 is an amino acid sequence of SEQ. ID. NO. 6, showing amino acid substitution sites for producing an IL-7A polypeptide. SEQ ID NO. 8 is a fragment IL-7A.

```
IL-7A.
                                                    SEQ ID NO. 1
ATG TTC CAT GTT TCT TTT AGG TAT ATC TTT GGA CTT CCT CCC CTG ATC CTT

GTT CTG TTG CCA GTA GCA TCA TCT GAT TGT GAT ATT GAA GGT AAA GAT GGC

AAA CAA TAT GAG AGT GTT CTA ATG GTC AGC ATC GAT CAA TTA TTG GAC AGC

ATG AAA GAA ATT GGT AGC AAT TGC CTG AAT AAT GAA TTT AAC TTT TTT AAA

AGA CAT ATC TGT GAT GCT AAT AAG GAA GGT ATG TTT TTA TTC CGT GCT GCT

CGC AAG TTG AGG CAA TTT CTT AAA ATG AAT AGC ACT GGT GAT TTT GAT CTC

CAC TTA TTA AAA GTT TCA GAA GGC ACA ACA ATA CTG TTG AAC TGC ACT GGC

CAG GTT AAA GGA AGA AAA CCA GCT GCC CTG GGT GAA GCC CAA CCA ACA

AAG AGT TTG GAA GAA AAT AAA TCT TTA AAG GAA CAG AAA AAA CTG AAT

GAC TTG TGT TTC CTA AAG AGA CTA TTA CAA GAG ATA AAA ACT TGT TGG AAT

AAA ATT TTG ATG GGC ACT AAA GAA CAC TGA

WT IL-7 amino acids number177
                                                    SEQ ID NO. 2
MFHVSFRYIF GLPPLILVLL PVASSDCDIE GKDGKQYESV LMVSIDQLLD SMKEIGSNCL

NNEFNFFKRH ICDANKEGMF LFRAARKLRQ FLKMNSTGDF DLHLLKVSEG TTILLNCTGQ

VKGRKPAALG EAQPTKSLEE NKSLKEQKKL NDLCFLKRLL QEIKTCWNKI LMGTKEH an IL-7A with T₉₇ to V, sited indicated by underlined in bold.
                                                    SEQ ID NO. 3
ATG TTC CAT GTT TCT TTT AGG TAT ATC TTT GGA CTT CCT CCC CTG ATC CTT

GTT CTG TTG CCA GTA GCA TCA TCT GAT TGT GAT ATT GAA GGT AAA GAT GGC

AAA CAA TAT GAG AGT GTT CTA ATG GTC AGC ATC GAT CAA TTA TTG GAC AGC

ATG AAA GAA ATT GGT AGC AAT TGC CTG AAT AAT GAA TTT AAC TTT TTT AAA

AGA CAT ATC TGT GAT GCT AAT AAG GAA GGT ATG TTT TTA TTC CGT GCT GCT

CGC AAG TTG AGG CAA TTT CTT AAA ATG AAT AGC GTT GGT GAT TTT GAT CTC

CAC TTA TTA AAA GTT TCA GAA GGC ACA ACA ATA CTG TTG AAC TGC ACT GGC

CAG GTT AAA GGA AGA AAA CCA GCT GCC CTG GGT GAA GCC CAA CCA ACA

AAG AGT TTG GAA GAA AAT AAA TCT TTA AAG GAA CAG AAA AAA CTG AAT

GAC TTG TGT TTC CTA AAG AGA CTA TTA CAA GAG ATA AAA ACT TGT TGG AAT

AAA ATT TTG ATG GGC ACT AAA GAA CAC TGA *CTCGAG*

Amino acid sequence encoded by SEQ ID NO. 3.
                                                    SEQ ID NO. 4
MFHVSFRYIF GLPPLILVLL PVASSDCDIE GKDGKQYESV LMVSIDQLLD SMKEIGSNCL

NNEFNFFKRH ICDANKEGMF LFRAARKLRQ FLKMNS_V_GDF DLHLLKVSEG
```

TTILLNCTGQ

VKGRKPAALG EAQPTKSLEE NKSLKEQKKL NDLCFLKRLL QEIKTCWNKI LMGTKEH

SEQ ID NO. 5

*GAATCC* ATG <u>TGG TGG CGC CTG TGG TGG CTG CTG CTG CTG CTG CTG CTG CTG</u>

<u>TGG CCC ATG GTG TGG GCC</u> TTC CAT GTT TCT TTT AGG TAT ATC TTT GGA CTT

CCT CCC CTG ATC CTT GTT CTG TTG CCA GTA GCA TCA TCT GAT TGT GAT ATT

GAA GGT AAA GAT GGC AAA CAA TAT GAG AGT GTT CTA ATG GTC AGC ATC

GAT CAA TTA TTG GAC AGC ATG AAA GAA ATT GGT AGC AAT TGC CTG AAT AAT

GAA TTT AAC TTT TTT AAA AGA CAT ATC TGT GAT GCT AAT AAG GAA GGT ATG

TTT TTA TTC CGT GCT GCT CGC AAG TTG AGG CAA TTT CTT AAA ATG AAT AGC

<u>GTT</u> GGT GAT TTT GAT CTC CAC TTA TTA AAA GTT TCA GAA GGC ACA ACA ATA

CTG TTG AAC TGC ACT GGC CAG GTT AAA GGA AGA AAA CCA GCT GCC CTG

GGT GAA GCC CAA CCA ACA AAG AGT TTG GAA GAA AAT AAA TCT TTA AAG

GAA CAG AAA AAA CTG AAT GAC TTG TGT TTC CTA AAG AGA CTA TTA CAA

GAG ATA AAA ACT TGT TGG AAT AAA ATT TTG ATG GGC ACT AAA GAA CAC

TGA *CTCGAG*

SEQ ID NO. 6

ATG TTC CAT GTT TCT TTT AGG TAT ATC TTT GGA CTT CCT CCC CTG ATC CTT

GTT CTG TTG CCA GTA GCA TCA TCT GAT TGT GAT ATT GAA GGT AAA GAT GGC

AAA CAA TAT GAG AGT GTT CTA ATG GTC AGC ATC GAT CAA TTA TTG GAC

AGC ATG AAA GAA ATT GGT AGC AAT TGC CTG AAT AAT GAA TTT AAC TTT TTT

AAA AGA CAT ATC TGT GAT GCT AAT AAG GAA GGT ATG TTT TTA TTC CGT GCT

GCT CGC AAG TTG AGG CAA TTT CTT AAA ATG AAT AGC ACT GGT GAT TTT GAT

CTC CAC TTA TTA AAA GTT TCA GAA GGC ACA ACA ATA CTG TTG AAC TGC

ACT GGC CAG GTT AAA GGA AGA AAA CCA GCT GCC CTG GGT GAA GCC CAA

CCA ACA AAG AGT TTG GAA GAA AAT AAA TCT TTA AAG GAA CAG AAA AAA

CTG AAT GAC TTG TGT TTC CTA AAG AGA CTA TTA CAA GAG ATA AAA ACT TGT

TGG AAT AAA ATT TTG ATG GGC ACT AAA GAA CAC TGA

SEQ ID NO. 7

MFHVSFRYIF GLPPLILVLL PVASSDCDIE GKDGKQYESV LMVSIDQLLD

SMKEIGSNCL

NNEFNFFKRH ICDANKEGMF LFRAARKLRQ FLKMNSTGDF DLHLLKVSEG

TTILLNCTGQ

VKGRKPAALG EAQPTKSLEE NKSLKEQKKL NDLCFLKRLL QEIKTCWNKI LMGTKEH

Sites for mutation in wt IL-7 include, but are not limited to, q36, s39, v40, v43, q47, t97, d99, L102, L105, k106, e109, g110, i113, and/or L114.

SEQ ID NO. 8 is a fragment of an IL-7A, missing at least 24 amino acids, possible amino acid substitution sites shown by bold, underlined font.

MDCDIE GKDGKQYESV LMVSIDQLLD SMKEIGSNCL

NNEFNFFKRH ICDANKEGMF LFRAARKLRQ FLKMNSTGDF

DLHLLKVSEG TTILLNCTGQ

-continued

VKGRKPAALG EAQPTKSLEE NKSLKEQKKL NDLCFLKRLL

QEIKTCWNKI LMGTKE

Mutations to form an IL-7A of the present invention may comprise:

Thr97 is substituted with Val q36, s39, v40, v43, q47, t97, d99, L102, L105, k106, e109, g110, i113, and/or L114 are sites on IL-7 that interact with the IL-7R and when mutated will reduce binding.

The mutations listed above were intended to disrupt binding of an IL-7A to IL-7R. Binding disruption may occur by substituting the target amino acid with an amino acid having different properties, such as positive charge, negative charge, no charge, hydrophobicity, polarity, etc. of the side chain. For example, positively charged amino acids are substituted with a negatively charged amino acid or with an amino acid that is hydrophobic, or an amino acid that is polar, or an amino acid that is not charged. Amino acid substitutions can be made by those skilled in art. To do so, the target amino acid is evaluated for its properties and replaced with an amino acid having a different property. Properties of positively and negatively charged amino acids are known to those skilled in the art.

Figure 5:
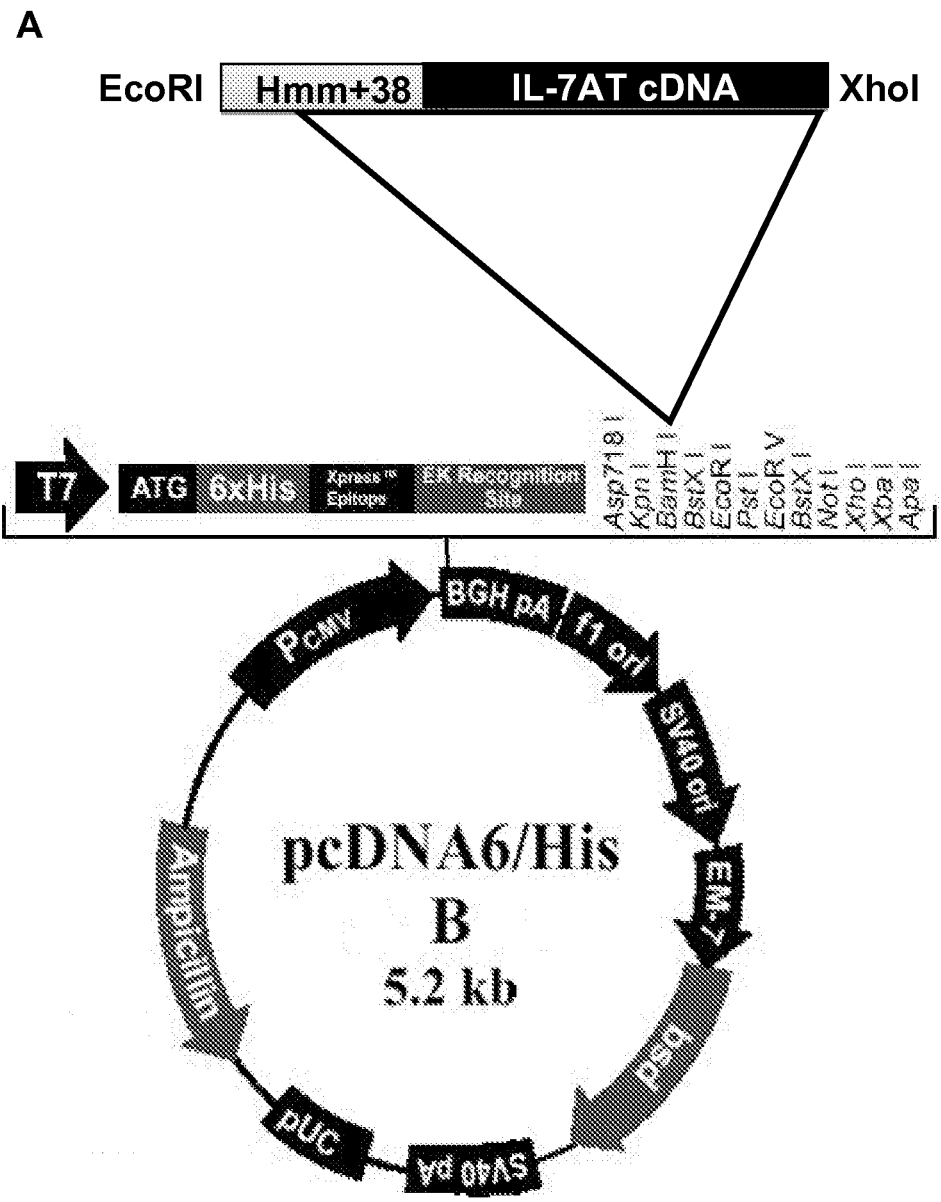
FIG. 5 shows generation of the HMM-IL-7AT plasmid.

A plasmid comprising an IL-7A was produced, as shown in FIG. 5. In order to express an IL-7A in a mammalian system, directed mutagenesis of IL-7 was performed to mutate the Threonine at position 97 to a Valine, see underlined in FIG. 5. Mutation was generated with the QuickChange II Site Directed Mutagenesis kit (Strategene). The mutated IL-7AT cDNA was then amplified using a forward primer containing an HMM sequence: (ATG) TGG TGG CGC CTG TGG TGG CTG CTG CTG CTG CTG CTG CTG CTG TGG CCC ATG GTG TGG GCC (SEQ ID NO: 9). The fusion protein was flanked by 5' EcoRI and 3' XhoI restriction sequences to allow for cloning into pcDNA6/His B vector for expression in mammalian system (Invitrogen). Sequencing was done to ensure proper orientation of the cDNA, retention of the mutation, and that the ATG start codon was on the HMM sequence to allow for accurate transcription.

The present invention comprises compositions comprising an IL-7A polypeptide. An aspect of the invention comprises compositions comprising a nucleic acid encoding SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or SEQ ID NO. 7 with one or more amino acid substitutions at sites q36, s39, v40, v43, q47, t97, d99, L102, L105, k106, e109, g110, i113, and/or L114 further comprising an HMM secretory element. An IL-7A, described by mutations of SEQ ID NO. 7, or its variants, described by other SEQ ID NOs disclosed herein, may be made by any method known for producing polypeptides. For example, the present invention comprises an IL-7A polypeptide that is a recombinant polypeptide. The present invention comprises an IL-7A that is a synthetic polypeptide. The present invention comprises an IL-7A polypeptide that has binding and/or biochemical characteristics of some or all of IL-7. Polypeptides disclosed herein that have binding characteristics different from those of IL-7 are referred to herein as IL-7A polypeptides.

Disclosed herein are inhibitors of IL-7. In an aspect, the IL-7 inhibitor is an IL-7A polypeptide. IL-7 inhibitors disclosed herein can be recombinant or synthetic polypeptides. Polypeptides may comprise SEQ ID NO. 7 with one or more amino acid substitutions at sites q36, s39, v40, v43, q47, t97, d99, L102, L105, k106, e109, g110, i113, and/or L114, or SEQ ID NOs 4 or 8, SEQ ID NO. 7 with one or more amino acid substitutions at sites q36, s39, v40, v43, q47, t97, d99, L102, L105, k106, e109, g110, i113, and/or L114, or SEQ ID NOs 4 or 8 or portions thereof.

The present invention comprises polypeptides that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to SEQ ID NO. 7, for example, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Disclosed herein are polypeptide variants that have 70-74, 75-79, 80-84, 85-89, 90-94, 95-99 percent homology to SEQ ID NO:7, for example, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Disclosed polypeptide variants comprise 70-99, 75-95, or 80-90 percent homology to SEQ ID NO. 7, SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, 113, and/or L114, or SEQ ID NOs 4 or 8, or 70-80, 80-90, or 90-99 percent homology to SEQ ID NO:7, or SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

An aspect of the present invention comprises a polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, i113, and/or L114, or SEQ ID NOs 4 or 8, and additional amino acids on the amino end of SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or on the carboxy end of SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or on both the amino end and the carboxy end of SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

Disclosed herein are fragments of an IL-7A, having at least one property of an IL-7A. For example SEQ ID NO. 8.

Disclosed herein are IL-7A polypeptides that have modulated IL-7 and/or that modulate IL-7R biochemical and binding properties. In an aspect, the disclosed polypeptide comprises SEQ ID NO. 7 with one or more amino acid substitutions at sites q36, s39, v40, v43, q47, t97, d99, L102, L105, k106, e109, g110, i113, and/or L114, or SEQ ID NOs 4 or 8 SEQ ID NO. 7 with one or more amino acid substitutions at sites q36, s39, v40, v43, q47, t97, d99, L102, L105, k106, e109, g110, i113, and/or L114, or SEQ ID NOs 4 or 8. An IL-7A polypeptide is not wildtype IL-7, in that the amino acid sequence is different in the two proteins.

Disclosed herein are polypeptides that are homologous to polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their peptide or nucleic acid sequences. Many of the methods for determining homology between two evolutionarily related molecules are routinely applied to any two or more nucleic acids or proteins for the purpose of measuring sequence similarity regardless of whether they are evolutionarily related or not. Thus, the polypeptides disclosed herein comprise polypeptides of multiple species, including but not limited to mouse, human, chicken, pig, rat, cow, chimpanzee, zebrafish, etc. Further, the disclosed IL-7R or IL-7A may be from multiple species, including but not limited to mouse, human, chicken, pig, rat, cow, chimpanzee, zebrafish, etc.

Polypeptides disclosed herein encompass naturally occurring or synthetic molecule, and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

Disclosed herein are multimers of one or more polypeptides disclosed herein. In an aspect, a multimer comprises more than one of the monomers disclosed herein. A disclosed multimer can be a dimmer, trimer, quatromer, quintomer, or the like, for example, 2-mer, 3-mer, 4-mer, 5-mer, etc of a polypeptide (1-mer). For example, in an aspect, the monomer comprises a sequence of 176 or 177 amino acids, such as the 177 amino acids of SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the monomer comprise a variant of SEQ ID NO:7, such as, for example, the sequence of SEQ ID NOs:4 or 8. In an aspect, the disclosed multimers comprise a combination of one or more monomers comprising SEQ ID NO:2 and one or more monomers comprising a variant of SEQ ID NO:7, such as SEQ ID NOs:4 or 8. Disclosed are compositions comprising the disclosed multimers, including compositions comprising monomers comprising the amino acid sequence of SEQ ID NO:2, 7, SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

Modifications to amino acids or polypeptides include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation.

Also, polypeptides disclosed herein can have one or more types of modifications. Numerous variants or derivatives of the peptides and analogs of the invention are also contemplated. As used herein, the term "analog" is used interchangeably with "variant" and "derivative." Variants and derivatives are well understood to those of skill in the art and can involve amino acid sequence modifications. Such amino acid sequence modifications typically fall into one or more of three classes: substitutional; insertional; or deletional variants.

Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog.

The polypeptides disclosed herein can comprise one or more substitutional variants, i.e., a polypeptide in which at least one residue has been removed and a different residue inserted in its place. Such substitutions generally are made in accordance with Table 2 and are referred to as conservative substitutions.

TABLE 1

Exemplary Conservative Amino Acid Substitutions

| Original Residue | Exemplary Conservative Substitutions |
| --- | --- |
| Ala | Ser |
| Arg | Gly, Gln |
| Asn | Gln; His |
| Asp | Glu |
| Cys | Ser |
| Gln | Asn, Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions that are generally expected to produce the greatest changes in the protein properties are those in which: (a) the hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or hystidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

Disclosed herein is an IL-7R (interleukin-7 receptor) ligand having properties that are modulated or attenuated, compared to wildtype IL-7, and for example, an IL-7A polypeptide comprises a native IL-7 polypeptide having an amino acid substitution at sites q36, s39, v40, v43, q47, t97, d99, L102, L105, k106, e109, g110, i113, and/or L114. An IL-7A polypeptide with attenuated properties can have one or more of the substitutions listed. Specifically, an IL-7A polypeptide can have any combination or permutation of the substitution sites q36, s39, v40, v43, q47, t97, d99, L102, L105, k106, e109, g110, i113, and/or L114. Furthermore, the IL-7A polypeptide can comprise substitutions not disclosed herein, but which either confer a desirable property to the IL-7A polypeptide, or have no negative impact on the IL-7A polypeptide.

By "attenuated signal" or "reduced binding" is meant that an IL-7A polypeptide has less than full binding strength or affinity for the IL-7R when compared to a native IL-7 molecule binding to IL-7R. This can mean that, compared to a native IL-7 molecule, an IL-7A polypeptide has 99, 98, 97, 96, 95, 94, 93, 92, 91, 90, 89, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1% binding strength or affinity to the IL-7 receptor, as compared to a native IL-7 molecule.

Mutations to the IL-7 polypeptide may or may not alter the binding site, and may or may not alter binding affinity, but may otherwise interfere with the binding of an IL-7A polypeptide to the IL-7R so as to achieve modulated binding which translates into a modulated or attenuated receptor signal.

In one example, one can use the nominal mass differences for single substitutions among the 20 common amino acids to determine substitutions (Table 2). This is not considered to be limiting, but rather to give an example of substitutions based on mass differences.

TABLE 2

| Δ Mass | Possible Substitutions |
|---|---|
| 129 | Trp -> Gly |
| 115 | Trp -> Ala |
| 106 | Tyr -> Gly |
| 99 | Arg -> Gly, Trp -> Ser |
| 92 | Tyr -> Ala |
| 90 | Phe -> Gly |
| 89 | Trp -> Pro |
| 87 | Trp -> Val |
| 85 | Arg -> Ala, Trp -> Thr |
| 83 | Trp -> Cys |
| 80 | His -> Gly |
| 76 | Tyr -> Ser, Phe -> Ala |
| 74 | Met -> Gly |
| 73 | Trp -> Ile/Leu |
| 72 | Trp -> Asn, Glu -> Gly |
| 71 | Lys/Gln -> Gly, Trp -> Asp |
| 69 | Arg -> Ser |
| 66 | Tyr -> Pro, His -> Ala |
| 64 | Tyr -> Val |
| 62 | Tyr -> Thr |
| 60 | Phe -> Ser, Met -> Ala, Tyr -> Cys |
| 59 | Arg -> Pro |
| 58 | Glu -> Ala, Asp -> Gly, Trp -> Lys/Gln |
| 57 | Lys/Gln -> Ala, Asn -> Gly, Arg -> Val, Trp -> Glu |
| 56 | Ile/Leu -> Gly |
| 55 | Arg -> Thr, Trp -> Met |
| 53 | Arg -> Cys |
| 50 | Phe -> Pro, His -> Ser, Tyr -> Ile/Leu |
| 49 | Tyr -> Asn, Trp -> His |

TABLE 2-continued

| Δ Mass | Possible Substitutions |
|---|---|
| 48 | Phe -> Val, Tyr -> Asp |
| 46 | Phe -> Thr, Cys -> Gly |
| 44 | Met -> Ser, Asp -> Ala, Thr -> Gly, Phe -> Cys |
| 43 | Asn -> Ala, Arg -> Ile/Leu |
| 42 | Val -> Gly, Ile/Leu -> Ala, Glu -> Ser, Arg -> Asn |
| 41 | Lys/Gln -> Ser, Arg -> Asp |
| 40 | Pro -> Gly, His -> Pro |
| 39 | Trp -> Phe |
| 38 | His -> Val |
| 36 | His -> Thr |
| 35 | Tyr -> Lys/Gln |
| 34 | Met -> Pro, His -> Cys, Phe -> Ile/Leu, Tyr -> Glu |
| 33 | Phe -> Asn |
| 32 | Cys -> Ala, Glu -> Pro, Met -> Val, Phe -> Asp, Tyr -> Met |
| 31 | Lys/Gln -> Pro |
| 30 | Ser -> Gly, Thr -> Ala, Glu -> Val, Met -> Thr, Trp -> Arg |
| 29 | Lys/Gln -> Val |
| 28 | Val -> Ala, Asp -> Ser, Glu -> Thr, Met -> Cys, Arg -> Lys/Gln |
| 27 | Asn -> Ser, Lys/Gln -> Thr, Arg -> Glu |
| 26 | Pro -> Ala, Ile/Leu -> Ser, Glu -> Cys, Tyr -> His |
| 25 | Lys/Gln -> Cys, Arg -> Met |
| 24 | His -> Ile/Leu |
| 23 | His -> Asn, Trp -> Tyr |
| 22 | His -> Asp |
| 19 | Phe -> Lys/Gln, Arg -> His |
| 18 | Asp -> Pro, Met -> Ile/Leu, Phe -> Glu |
| 17 | Asn -> Pro, Met -> Asn |
| 16 | Ser -> Ala, Cys -> Ser, Ile/Leu -> Pro, Asp -> Val, Glu -> Ile/Leu, Met -> Asp, Phe -> Met, Tyr -> Phe |
| 15 | Asn -> Val, Lys/Gln -> Ile/Leu, Glu -> Asn |
| 14 | Ala -> Gly, Thr -> Ser, Ile/Leu -> Val, Asp -> Thr, Glu -> Asp, Lys/Gln -> Asn |
| 13 | Asn -> Thr, Lys/Gln -> Asp |
| 12 | Val -> Ser, Ile/Leu -> Thr, Asp -> Cys |
| 11 | Asn -> Cys |
| 10 | Pro -> Ser, Ile/Leu -> Cys, Phe -> His |
| 9 | His -> Lys/Gln, Arg -> Phe |
| 8 | His -> Glu |
| 7 | Tyr -> Arg |
| 6 | Cys -> Pro, His -> Met |
| 4 | Thr -> Pro, Cys -> Val |
| 3 | Met -> Lys/Gln |
| 2 | Val -> Pro, Thr -> Val, Cys -> Thr, Asp -> Ile/Leu, Met -> Glu |
| 1 | Asn -> Ile/Leu, Asp -> Asn, Glu-Lys/Gln |
| 1 | Ile/Leu -> Asn, Asn -> Asp, Lys/Gln -> Glu |
| 2 | Pro -> Val, Val -> Thr, Thr -> Cys, Ile/Leu -> Asp, Glu -> Met |
| 3 | Lys/Gln -> Met |
| 4 | Pro -> Thr, Val -> Cys |
| 6 | Pro -> Cys, Met -> His |
| 7 | Arg -> Tyr |
| 8 | Glu -> His |
| 9 | Lys/Gln -> His, Phe -> Arg |
| 10 | Ser -> Pro, Cys -> Ile/Leu, His -> Phe |
| 11 | Cys -> Asn |
| 12 | Ser -> Val, Thr -> Ile/Leu, Cys -> Asp |
| 13 | Thr -> Asn, Asp -> Lys/Gln |
| 14 | Gly -> Ala, Ser -> Thr, Val -> Ile/Leu, Thr -> Asp, Asn-Lys/Gln, Asp -> Glu |
| 15 | Val -> Asn, Ile/Leu -> Lys/Gln, Asn -> Glu |
| 16 | Ala -> Ser, Ser -> Cys, Pro -> Ile/Leu, Val -> Asp, Ile/Leu -> Glu, Asp -> Met, Met -> Phe, Phe -> Tyr |
| 17 | Pro -> Asn, Asn -> Met |
| 18 | Pro -> Asp, Ile/Leu -> Met, Glu -> Phe |
| 19 | Lys/Gln -> Phe, His -> Arg |
| 22 | Asp -> His |
| 23 | Asn -> His, Tyr -> Trp |
| 24 | Ile/Leu -> His |
| 25 | Cys -> Lys/Gln, Met -> Arg |
| 26 | Ala -> Pro, Ser -> Ile/Leu, Cys -> Glu, His -> Tyr |
| 27 | Ser -> Asn, Thr -> Lys/Gln, Gly -> Arg |
| 28 | Ala -> Val, Ser -> Asp, Thr -> Glu, Cys -> Met, Lys/Gln -> Arg |
| 29 | Val -> Lys/Gln |
| 30 | Gly -> Ser, Ala -> Thr, Val -> Glu, Thr -> Met, Arg -> Trp |
| 31 | Pro -> Lys/Gln |
| 32 | Ala -> Cys, Pro -> Glu, Val -> Met, Asp -> Phe, Met -> Tyr |
| 33 | Asn -> Phe |
| 34 | Pro -> Met, Cys -> His, Ile/Leu -> Phe, Glu -> Tyr |
| 35 | Lys/Gln -> Tyr |

TABLE 2-continued

| Δ Mass | Possible Substitutions |
|---|---|
| 36 | Thr -> His |
| 38 | Val -> His |
| 39 | Phe -> Trp |
| 40 | Gly -> Pro, Pro -> His |
| 41 | Ser -> Lys/Gln, Asp -> Arg |
| 42 | Gly -> Val, Ala -> Ile/Leu, Ser -> Glu, Asn -> Arg |
| 43 | Ala -> Asn, Ile/Leu -> Arg |
| 44 | Gly -> Thr, Ala -> Asp, Ser -> Met, Cys -> Phe |
| 46 | Gly -> Cys, Thr -> Phe |
| 48 | Val -> Phe, Asp -> Tyr |
| 49 | Asn -> Tyr, His -> Trp |
| 50 | Ser -> His, Pro -> Phe, Ile/Leu -> Tyr |
| 53 | Cys -> Arg |
| 55 | Thr -> Arg, Met -> Trp |
| 56 | Gly -> Ile/Leu |
| 57 | Gly -> Asn, Ala -> Lys/Gln, Val -> Arg, Glu -> Trp |
| 58 | Gly -> Asp, Ala -> Glu, Lys/Gln -> Trp |
| 59 | Pro -> Arg |
| 60 | Ala -> Met, Ser -> Phe, Cys -> Tyr |
| 62 | Thr -> Tyr |
| 64 | Val -> Tyr |
| 66 | Ala -> His, Pro -> Tyr |
| 69 | Ser -> Arg |
| 71 | Gly -> Lys/Gln, Asp -> Trp |
| 72 | Gly -> Glu, Asn -> Trp |
| 73 | Ile/Leu -> Trp |
| 74 | Gly -> Met |
| 76 | Ala -> Phe, Ser -> Tyr |
| 80 | Gly -> His |
| 83 | Cys -> Trp |
| 85 | Ala -> Arg, Thr -> Trp |
| 87 | Val -> Trp |
| 89 | Pro -> Trp |
| 90 | Gly -> Phe |
| 92 | Ala -> Tyr |
| 99 | Gly -> Arg, Ser -> Trp |
| 106 | Gly -> Tyr |
| 115 | Ala -> Trp |
| 129 | Gly -> Trp |

Polypeptides of the present invention are produced by any method known in the art. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry. A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively. Alternatively, the peptide or polypeptide is independently synthesized in vivo. Once isolated, these independent peptides or polypeptides may be linked to form a peptide or fragment thereof via similar peptide condensation reactions.

For example, enzymatic ligation of cloned or synthetic peptide segments allow peptide fragments to be joined to produce larger peptide fragments, polypeptides or whole protein domains. Alternatively, native chemical ligation of synthetic peptides can be utilized to synthetically construct larger peptides or polypeptides from shorter peptide fragments. This method consists of a two-step chemical reaction. The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolim et al., 1992; Clark-Lewis et al., 1994; Clark-Lewis et al., 1991; Rajarathnam et al., 1994).

Alternatively, unprotected peptide segments are chemically linked where the bond formed between the peptide segments as a result of the chemical ligation is an unnatural (non-peptide) bond (Schnolzer et al., 1992). This technique has been used to synthesize analogs of protein domains as well as large amounts of relatively pure proteins with full biological activity (deLisle et al., 1992).

Also disclosed are methods for generating the disclosed peptides and polypeptides in vivo. For example, in an aspect, the disclosed peptides of the present invention are translation products of nucleic acids. In an aspect, nucleic acids are introduced into cells, and the cells express nucleic acids, which are translated to form the disclosed peptides. The present invention also provides for a host cell comprising a nucleic acid encoding one or more of the disclosed peptides. In an aspect, bacterial, yeast, Dictyostelium discoideum, insect, and mammalian cell expression systems can be used to produce the peptides of the present invention. The disclosed peptides can be used as human and animal therapeutics. The art is familiar with expression systems that produce, in an efficient and inexpensive manner, large quantities of soluble, desirable peptide products.

Such an expression system comprises host cells, which can be eukaryotic cells or prokaryotic cells. In the case of eukaryotic cells, retrovirus or adenovirus based vectors can be used to put the nucleic acid or the invention into the host cell. Methods known to one of skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation tranfection methods.

Host cells can be obtained from commercial sources such as the American Type Culture Collection (ATCC). Host cells can be grown in liquid media culture or on tissue culture plates. The growth conditions will be dependent upon the specific host cells used and such conditions would be known to one of skill in the art. Transfection and growth of host cells is described in Maniatis et al. The invention provides for a recombinant cell expressing a heterologous or homologous nucleic acid encoding the peptide of the claimed invention. The invention also provides for host cell producing a recombinant polypeptide of the invention.

Disclosed peptides generated during in vivo cultivation can be collected using conventional purification and separation techniques, such as salting out, dialysis, filtration, centrifugation, concentration and lyopholization. If a further purified peptide preparation is desirable, then a peptide preparation of the highest purity can be obtained by the above mentioned techniques in combination with more sensitive conventional purification and separation techniques, such as adsorption and desorption with ion exchange resin, gel filtration, affinity chromatography, isoelectric point fractionation, electrophoresis, etc. Examples herein teach a method of purification of an IL-7A.

The present invention comprises methods and compositions comprising polypeptides that have a modulated binding to IL-7R. The present invention comprises methods and compositions comprising a polypeptide, IL-7A, that competes with IL-7 for binding sites for IL-7R. An example of a polypeptide of the present invention is SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

Disclosed herein are polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. One of ordinary skill in the art at the time of the invention would have understood that other variations can occur in the sequence of SEQ ID NO. 2, or SEQ ID NO. 7 with one or more amino acid substitutions at sites 37, 38, 41, 42, 45, 49, 61, 88, and/or 90, or SEQ ID NOs 4, 8, 9 or 10. Some variations do not affect its functionality, while others affect the functionality, such as binding or solubility. Specifically disclosed are peptide variants that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Disclosed are peptide variants that have 70-74, 75-79, 80-84, 85-89, 90-94, 95-99 percent homology to SEQ ID NO:2, or SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Disclosed peptide variants comprise 70-99, 75-95, or 80-90 percent homology to SEQ ID NO:2, or SEQ ID NO. 7 with one or more amino acid substitutions at sites q36, s39, v40, v43, q47, t97, d99, L102, L105, k106, e109, g110, i113, and/or L114, or SEQ ID NOs 4, 8; or 70-80, 80-90, or 90-100 percent homology to SEQ ID NO:2, or SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

Those of skill in the art readily understand how to determine the homology between two or more proteins or two or more nucleic acids. For example, the homology can be calculated after aligning the two sequences so that the homology is at its highest level. Another way of calculating homology can be performed by published algorithms. Optimal alignment of sequences for comparison may be conducted by the local homology algorithm of Smith et al., 1981, by the homology alignment algorithm of Needleman et al., 1970, by the search for similarity method of Pearson et a., 1988, by computerized implementations of these algorithms (GAP, BEST-FIT, FASTA, and TFASTA in the Wisconsin Genetics Software Package, Genetics Computer Group, 575 Science Dr., Madison, Wis.), or by inspection.

The present invention comprises methods and compositions comprising an IL-7A polypeptide comprising modified amino acids. In an aspect, the polypeptide comprises at least one modified amino acid. For example, a polypeptide comprising the sequence of SEQ ID NO:2, SEQ ID NO. 7 with one or more amino acid substitutions at sites q36, s39, v40, v43, q47, t97, d99, L102, L105, k106, e109, g110, i113, and/or L114, or SEQ ID NOs 4 or 8 can comprise one or more modified amino acids. In an aspect, a polypeptide is modified at the amino terminus or at the carboxy terminus. In an aspect, both the amino and carboxy termini are modified. In an aspect, a polypeptide comprises at least one modified amino acid that is not at the carboxy or amino termini.

The present invention comprises methods and compositions comprising an IL-7A polypeptide comprising at least one label. The disclosed compositions and polypeptides can, for example, be labeled so that the label or moiety that can be selectively detected, such as in an assay. Examples include without limitation, radiolabels, (e.g., $^3H$, $^{14}C$, $^{35}S$, $^{125}I$, $^{131}I$), affinity tags (e.g., biotin/avidin or streptavidin, binding sites for antibodies, metal binding domains, epitope tags, FLASH binding domains (U.S. Pat. Nos. 6,451,569, 6,054,271, 6,008,378, and 5,932,474 discussing glutathione or maltose binding domains), fluorescent or luminescent moieties (e.g., fluorescein and derivatives, GFP, rhodamine and derivatives, lanthanides etc.), and enzymatic moieties (e.g., horseradish peroxidase, beta-galactosidase, beta-lactamase, luciferase, alkaline phosphatase). Such detectable labels can be formed in situ, for example, through use of an unlabeled primary antibody which can be detected by a secondary antibody having an attached detectable label.

The present invention comprises methods and compositions comprising an isolated nucleic acid encoding one or more IL-7A polypeptides, or fragments thereof. In an aspect, the isolated nucleic acid encodes an IL-7A polypeptide. In an aspect, the nucleic acid encodes a polypeptide with the amino acid sequence of SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the nucleic acid encodes a polypeptide disclosed herein. Disclosed herein is an isolated nucleic acid encoding an IL-7A polypeptide that is cell membrane permeable. In an aspect, the cell membrane permeable polypeptide encoded by the isolated nucleic acid is distributed throughout a cell, and can be, for example, co-localized to the nucleus of a cell or co-localized at the plasma membrane, and maybe excreted from a cell.

The present invention comprises methods and compositions comprising vectors encoding an IL-7A polypeptide. Disclosed are expression vectors useful in eukaryotic host cells (yeast, fungi, insect, plant, animal, human or nucleated cells) which can also contain sequences necessary for the termination of transcription which may affect mRNA expression. Disclosed vectors comprise a nucleic acid encoding an IL-7A. In an aspect, the nucleic acid of the vector encodes an IL-7A polypeptide. In an aspect, the vector comprises a sequence encoding a secretory peptide, including, but not limited to, HMM. In an aspect, nucleic acid of the vector encodes a IL-7A comprising a polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the nucleic acid of the vector encodes an IL-7A polypeptide comprising at SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the vector comprises a nucleic acid encoding an IL-7A polypeptide that is at least 75 percent homologous to SEQ ID NO:2, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the homology of the disclosed IL-7A polypeptide is at least 70-80, or 80-90, or 90-100 percent homologous to SEQ ID NO:2, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the homology of the disclosed IL-7A polypeptide is at least 75, 80, 85, 90, 95, 96, 97, 98, or 99 percent homologous to SEQ ID NO:2, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Nucleic acids encoding an IL-7A polypeptide include, but are not limited to, SEQ ID NO. 3 or 6 with one or more nucleic acid base changes at the indicated sites.

The present invention comprises methods and compositions comprising an isolated nucleic acid encoding any one or more of the polypeptides disclosed herein. In an aspect, the nucleic acid comprises DNA, RNA, and/or cDNA. It would be routine for one with ordinary skill in the art to make a nucleic acid that encodes the polypeptides disclosed herein since codons for each of the amino acids that make up the polypeptides are known. As non-limiting examples, the nucleic acids of the invention can be produced by recombinant, in vitro methods, or by chemical synthetic means using machines and standard chemistry which would be known to one of skill in the art, or by in vivo cellular synthesis. Methods of synthesizing nucleic acids would be well known to one of skill in the art, e.g., U.S. Pat. No. 6,472,184 and U.S. Pat. No. 6,444,111. These references are hereby incorporated by reference in their entireties.

Additionally, the invention provides a vector comprising the nucleic acid encoding any one or more of the polypeptides and peptides described herein. In an aspect, the invention provides a vector comprising a nucleic acid encoding at least one of the polypeptides of the present invention, e.g., SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, the invention provides a vector comprising a nucleic acid encoding a variant polypeptides of the present invention, e.g., a variant of SEQ ID NO:2, SEQ ID NO. 7 with one or more amino acid substitutions at sites q36, s39, v40, v43, q47, t97, d99, L102, L105, k106, e109, g110, i113, and/or L114, or SEQ ID NOs 4 or 8. The vector can be a viral vector, a plasmid vector, a cosmid vector, an adenoviral vector, a phage vector, a retroviral vector, an adeno-associated viral (AAV) vector, or any other vector capable of including a nucleic acid encoding a peptide or polypeptide of the invention. The vector can be an expression vector that is intended and capable of integrating into a cell genome. Other useful virus vectors include retroviruses such as Moloney murine leukemia virus (MoMuLV); papovaviruses such as JC, SV40, polyoma, adenoviruses; Epstein-Barr Virus (EBV); papilloma viruses, e.g., bovine papilloma virus type 1 (BPV); vaccinia and poliovirus and other human and animal viruses.

Preferred promoters controlling transcription from vectors in mammalian host cells may be obtained from various sources, for example, the genomes of viruses such as: polyoma, Simian Virus 40 (SV40), adenovirus, retroviruses, hepatitis B virus and cytomegalovirus, or from heterologous mammalian promoters, e.g., beta actin promoter. The early and late promoters of the SV40 virus are conveniently obtained as an SV40 restriction fragment which also contains the SV40 viral origin of replication. The immediate early promoter of the human cytomegalovirus is conveniently obtained as a HindIII E or Sau3A restriction fragment. Promoters from the host cell or related species are useful herein.

Whether heterologous or homologous, enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene.

Whether homologous or heterologous, a promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The disclosed vectors can comprise elements (such as, for example, promoters, enhancers, 3'-UTRs, LTRS, etc.) that are heterologous or homologous to the nucleic acid encoding a disclosed polypeptide of the present invention. The skilled person is familiar with the compositions and methods used to construct vectors comprising heterologous and homologous elements, such as, for example, a promoter, or enhancer, or 3'UTR, or LTR, or etc. that is homologous or heterologous to the sequence encoding the nucleic acid of interest.

The vectors used in host cells contain all or a part of a viral genome, such as long term repeats ("LTRs"), promoters (e.g., CMV promoters, SV40 promoter, RSV promoter), enhancers, and so forth. A non-limiting example of such adenoviruses which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F). When the host cell is a prokaryote, bacterial viruses, or phages, can be used to deliver the nucleic acid of the invention to the host cell. A non-limiting example of such vectors are vectors based upon, for example, lambda phage. In any case, the vector may comprise elements of more than one virus. The vector may additionally comprise a gene encoding a marker or reporter molecule to more easily trace expression of the vector.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

The present invention comprises host cells comprising one or more IL-7A polypeptides. In an aspect, host cells comprise an isolated nucleic acid encoding an IL-7A polypeptide. In an aspect, host cells comprise a nucleic acid encoding a polypeptide with the amino acid sequence of SEQ ID NO. 7 with one or more amino acid substitutions at sites q36, s39, v40, v43, q47, t97, d99, L102, L105, k106, e109, g110, i113, and/or L114, or SEQ ID NOs 4 or 8, and in an aspect, the nucleic acid encodes a polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Disclosed are host cells comprising a nucleic acid encoding a recombinant polypeptide. In an aspect, the recombinant polypeptide is an IL-7A polypeptide. Disclosed are host cells comprising IL-7 Apolypeptides.

In an aspect, host cells of the present invention may comprise an isolated nucleic acid encoding an IL-7A polypeptide that is cell membrane permeable. In an aspect, host cells comprise an isolated nucleic acid encoding an IL-7A polypeptide. In an aspect, the cell membrane is a plasma membrane. In an aspect, the cell membrane is a cytoplasmic membrane. In an aspect, the cell membrane is a nuclear membrane.

Compositions disclosed herein, including but not limited to, IL-7A polypeptides, or antibodies that specifically bind to IL-7A polypeptides disclosed herein, can be used therapeutically in combination with a pharmaceutically acceptable carrier. Suitable carriers and their formulations are described in Remington 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid and phosphoric acid, and/organic acids such as formic acid, acetic acid, propionic acid, glycolic acid, lactic acid, pyruvic acid, oxalic acid, malonic acid, succinic acid, maleic acid and fumaric acid, or by reaction with an inorganic base such as sodium hydroxide, ammonium hydroxide, and potassium hydroxide, and/organic bases such as mono-, di-, trialkyl and aryl amines and substituted ethanolamines.

The present invention comprises methods and compositions comprising a monoclonal antibody that specifically binds to an IL-7A polypeptide or an antigenic portion thereof. Compositions comprise antibodies, whether polyclonal or monoclonal, or fragments or subunits of antibodies, that specifically bind to an IL-7A polypeptide, to polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein. In an aspect, an antibody binds to an IL-7A polypeptide. In an aspect, an antibody binds to a synthetic IL-7A polypeptide. The present invention comprises a monoclonal or polyclonal antibody that specifically binds to an IL-7A polypeptide. In an aspect, the antibody can bind to a polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4, 8, or portions thereof.

The present invention comprises methods and compositions for diagnosing the immune status of a subject by determining the level of IL-7 or IL-7A or IL-7R comprising using a monoclonal antibody to determine the levels of IL-7 or IL-7A or IL-7R in a sample, subject, or patient. In an aspect, the monoclonal antibody binds to a polypeptide of SEQ ID NO. 7 with one or more amino acid substitutions at sites q36, s39, v40, v43, q47, t97, d99, L102, L105, k106, e109, g110, i113, and/or L114, or SEQ ID NOs 4 or 8. The present invention comprises methods and compositions for diagnosing the immune status of a subject comprising using polyclonal antibodies to determine the levels of IL-7 or IL-7A or IL-7R in a sample, subject, or patient. In an aspect, the polyclonal antibodies binds to a polypeptide of SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with an IL-7A polypeptide disclosed herein. For example, in an aspect, an antibody binds to or interacts with the polypeptide-represented by SEQ ID NO. 7 with one or more amino acid substitutions at sites q36, s39, v40, v43, q47, t97, d99, L102, L105, k106, e109, g110, i113, and/or L114, or SEQ ID NOs 4 or 8. The present invention comprises antibodies that bind to or interact with a portion of SEQ ID NO. 7 with one or more amino acid substitutions at sites q36, s39, v40, v43, q47, t97, d99, L102, L105, k106, e109, g110, i113, and/or L114, or SEQ ID NOs 4 or 8. In an aspect, an antibody binds to or interacts to an IL-7A polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. The present invention comprises assays using monoclonal, polyclonal or binding fragment of antibodies that bind to a portion of SEQ ID NO. 7 with one or more amino acid substitutions at sites q36, s39, v40, v43, q47, t97, d99, L102, L105, k106, e109, g110, i113, and/or L114, or SEQ ID NOs 4 or 8.

The present invention comprises methods and compositions comprising methods of treating cells to increase growth, survival and/or a potent immune response, comprising exposing cells to an IL-7A polypeptide that, upon binding to an IL-7R produces an attenuated signal by the IL-7R, under conditions to achieve growth, survival or an immune response. In a more specific embodiment, methods comprise exposing cells to an IL-7A polypeptide, in vitro or ex vivo, under conditions such that the IL-7A polypeptide comes into contact with the cells. The term in vitro is intended to encompass the term ex vivo, the latter being intended for the more specific situation where cells are removed from a subject and exposed to an IL-7A polypeptide outside the subject, with the further intention of being returned to the subject or another subject.

Disclosed herein are methods of identifying IL-7A polypeptides possessing an attenuated IL-7R induction signal, the method comprising: substituting an amino acid at a targeted site in the native IL-7 sequence to produce a variant IL-7 ligand; determining effect of binding of said variant IL-7 ligand to IL-7R; whereby a variant IL-7A ligand having a modulated, either lower or higher, binding affinity or avidity relative to the native IL-7 protein is identified as an attenuated IL-7AR agent.

In an example of this method, the substitution is not in the IL-7R binding site of the IL-7 polypeptide. In another example, the substitution may be within the IL-7R binding site. One of skill in the art will readily appreciate how to create a IL-7R ligand with the desired attenuated signal, as disclosed above. Also disclosed is an attenuated IL-7R ligand identified according to a method disclosed above.

Methods of the present invention comprise treating cells to increase growth, survival and/or a potent immune response, a method comprising exposing cells to an IL-7A peptide possessing an attenuated binding to an IL-7R, under conditions to achieve growth, survival or an immune response.

By "increasing growth or survival" is meant that an IL-7A polypeptide increases growth or survival of the cells by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, or 10 fold, or more, when compared to native IL-7 molecule. The cells can be CD-4 cells, for example.

By "increasing potent immune response" is meant that an IL-7A polypeptide increases the ability of the cell to put forth an immune response. This can mean that the cell is able to respond faster or for a longer duration, or that the response is more potent, meaning more effective overall. The response can be increased by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, or 10 fold, or more, when compared to native IL-7 molecule. The cells can be CD4 cells, for example.

The cells in methods disclosed herein can be obtained from a patient, and optionally frozen prior to exposure to an IL-7A polypeptide. One of skill in the art will appreciate the conditions under which such cells can be obtained and stored prior to use in the methods disclosed herein. Once the cells have been obtained, they can be exposed to an IL-7A polypeptide, ex vivo, under culture conditions with culture media containing an IL-7A polypeptide, for example. As described above, the cells can be CD4 cells, and can be obtained from bone marrow, by example.

Methods may comprise treating an immunodeficiency in a patient, comprising administering cells to said patient with cells produced according to the methods disclosed herein. A method may comprise administering a therapeutically effective amount of a compositions comprising an IL-7A polypeptide to a subject with an immunodeficiency, and improving the immune status of the subject. Methods may comprise administering immune cells, stem cells, or cells comprising IL-7A polypeptides or IL-7R, in conjunction, at the same time, following or sequentially, with IL-7A polypeptide compositions disclosed herein.

By "immunodeficiency" is meant a state in which the immune system's ability to fight infectious disease is compromised or entirely absent. Immunodeficiency may also decrease cancer immunosurveillance. Most cases of immunodeficiency are acquired ("secondary") but some people are born with defects in their immune system, or primary immunodeficiency. Transplant patients take medications to suppress their immune system as an anti-rejection measure, as do some patients suffering from an over-active immune system. A person who has an immunodeficiency of any kind is said to be immunocompromised. An immunocompromised person may be particularly vulnerable to opportunistic infections, in addition to normal infections that could affect everyone.

Examples of immunodeficiency include humoral immune deficiency, with signs or symptoms depending on the cause, but generally include signs of hypogammaglobulinemia (decrease of one or more types of antibodies) with presentations including repeated mild respiratory infections, and/or agammaglobulinemia (lack of all or most antibody production) which results in frequent severe infections and is often fatal. Another example is a T cell deficiency, often caused secondary disorders such as acquired immune deficiency syndrome. A further example is granulocyte deficiency, including decreased numbers of granulocytes (called granulocytopenia or, if absent, agranulocytosis) such as of neutrophil granulocytes (termed neutropenia). Granulocyte deficiencies also include decreased function of individual granulocytes, such as in chronic granulomatous disease. Another example is asplenia, where there is no function of the spleen. Complement deficiency is where the function of the complement system is deficient. In reality, immunodeficiency often affects multiple components, with notable examples including severe combined immunodeficiency (which is primary) and acquired immune deficiency syndrome (which is secondary).

A patient may have depleted bone marrow cells. For example, the patient may have undergone radiation or chemotherapy.

Methods of the present invention comprise inducing proliferation of immune cells in a subject in need thereof, comprising administering a therapeutically effective amount of a composition comprising an IL-7A polypeptide with attenuated binding affinity or avidity, as disclosed herein.

By "inducing proliferation of immune cells" is meant that the amount of immune cells is increased when compared to the amount of immune cells created when compared to native IL-7 molecule. For example, the amount of immune cells can be increased by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, or 10 fold, or more.

By "therapeutically effective amount" is to that amount of an IL-7A polypeptide sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one example, a method of inducing immune cell proliferation in a patient by administering an IL-7A polypeptide with attenuated signal can further comprise co-administering a therapeutically effective amount of stem cells. Such stem cells can be autologous or allogeneic. They can be treated by the methods disclosed herein.

Disclosed herein are methods of increasing immune cell reconstitution following stem cell transplantation in a patient, comprising administering a composition comprising a therapeutically effective amount of an IL-7A possessing attenuated binding affinity or avidity to the patient.

By "increasing immune cell reconstitution" is meant that following stem cell transplantation in a patient, the immune cells are able to reconstitute 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, or 10 fold, or more, faster than that of native IL-7 molecule alone.

The present invention comprises methods and compositions for diagnosing the effectiveness of a stem cell transplantation in a subject by determining the presence or amount of an IL-7A polypeptide in a subject to whom an IL-7A polypeptide was co-administered with the stem cells. The present invention comprises methods of detecting an IL-7A polypeptide in a sample from of a subject. The method may comprise detectably labeled IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise use of an antibody or fragment thereof to an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof.

The present invention comprises methods and compositions for diagnosing immune status in a subject, for example, motility of immune cells, by determining the presence or amount of an IL-7A polypeptide in a subject to whom an IL-7A polypeptide was co-administered with the stem cells. The present invention comprises methods of detecting an IL-7A polypeptide in a sample from of a subject. The method may comprise detectably labeled IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise use of an antibody or fragment thereof to an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof.

The term "subject" means any individual who is the target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. Subject includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The present invention comprises methods and compositions for determining the effectiveness of treatment with an IL-7A polypeptide in a subject comprising determining the presence or amount of an IL-7A polypeptide in a subject to whom an IL-7A polypeptide was administered. The present invention comprises methods of detecting an IL-7A polypeptide in a sample from of a subject. The method may comprise detectably labeled IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise use of an antibody or fragment thereof to an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof.

The present invention comprises assays for detecting the presence or amount of an IL-7A polypeptide in a sample. The present invention comprises methods of detecting an IL-7A polypeptide in a sample from of a subject. The method may comprise detectably labeled IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise use of an antibody or fragment thereof to an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof.

The present invention comprises methods and compositions for treating GVHD in a subject by administering an IL-7A polypeptide. The method may comprise one or more IL-7A polypeptides, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof.

The present invention comprises methods and compositions for treating an IL-7 related disease or condition in a subject, wherein the disease or condition is affected by an undesired level of IL-7, comprising administering a therapeutically effective amount of a composition comprising IL-7A. The method may comprise IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. After administration, the subject's condition or disease is treated or alleviated.

The present invention comprises methods and compositions for modulating immune responses in a subject. The present invention comprises methods of treating an immune response in a subject, comprising, administering to the subject an effective amount of a composition comprising an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise determining a change in the level of IL-7 or IL-7A or IL-7R, a change in the immune response, or other changes. Methods may further comprise administering other therapeutic agents in conjunction, at the same time, following or sequentially, with treatment of the immune response with an IL-7A polypeptide composition disclosed herein. The composition may be provided to a cell, to a composition, to an assay, to a subject, or to a sample from a subject.

The present invention comprises methods and compositions for modulating gene expression in a subject, in an assay, in a cell, or a sample from a subject. For example, the present invention comprises methods of modulating gene expression in a subject, comprising, administering to the subject an effective amount of a composition comprising an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise determining a change in the level of IL-7 or IL-7A or IL-7R, a change in gene expression, or other changes. Methods may further comprise administering therapeutic agents in conjunction, at the same time, following or sequentially, with modulating gene expression with IL-7A polypeptide compositions disclosed herein.

The present invention comprises methods and compositions modulating cellular development in a subject, in an assay, in a cell, or a sample from a subject. For example, the present invention comprises methods of modulating cellular development in a subject, comprising, administering to the subject an effective amount of a composition comprising an IL-7A polypeptide, or polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or other polypeptides and/or sequences disclosed herein, or combinations thereof. The method may comprise determining a change in the level of IL-7 or IL-7A or IL-7R proteins, a change in the cellular development, or other changes. Methods may further comprise administering therapeutic agents in conjunction, at the same time, following or sequentially, with modulating cellular development with IL-7A polypeptide compositions disclosed herein.

Also disclosed according to the present invention is a kit or system utilizing any one of the methods, selection strategies, materials, or components described herein, for example, comprising compositions comprising a nucleic acid encoding a polypeptide comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8, or one or more polypeptides comprising SEQ ID NO. 7 with one or more amino acid substitutions at sites q36, s39, v40, v43, q47, t97, d99, L102, L105, k106, e109, g110, i113, and/or L114, or SEQ ID NOs 4 or 8. Exemplary kits according to the present disclosure will optionally, additionally include instructions for performing methods or assays, packaging materials, one or more containers which contain an assay, a device or system components, or the like.

The present invention comprises methods and compositions comprising an isolated IL-7A protein, comprising SEQ ID NO. 7 having one or more amino acid substitutions at sites q36, s39, v40, v43, q47, t97, d99, L102, L105, k106, e109, g110, i113, or L114, wherein the IL-7A protein is not IL-7. In an aspect the binding of the IL-7A protein to an IL-7 receptor causes an attenuated signal by the receptor. The IL-7A protein may have an amino acid substitution at t97, which in aspects, is valine. The present invention comprises a method of identifying proteins that cause an attenuated IL-7R induction signal, comprising, substituting an amino acid at a targeted site in a native IL-7 sequence to produce an IL-7A protein; contacting cells comprising an IL-7R; and determining the affect of the IL-7A protein on the IL-7R response. The method comprises substituting that avoids the IL-7R binding site of the IL-7 sequence. In aspects, the IL-7R response does not result in a reduced number of IL-7R. The invention comprises an IL-7A protein identified according to the method disclosed.

The present invention comprises a method of treating cells to increase growth, survival and/or a potent immune response, comprising, contacting cells with an IL-7A protein under conditions to achieve growth, survival or an immune response. In an aspect, the cells are obtained from a subject. In an aspect, the cells are exposed to the IL-7A protein, ex vivo, under culture conditions. The cells may be CD4 cells. The cells may be bone marrow derived cells.

The present invention comprises an isolated nucleic acid encoding an IL-7A protein having an amino acid sequence as set forth in SEQ ID. NO.: 7, wherein one or more amino acids are substituted at q36, s39, v40, v43, q47, t97, d99, L102, L105, k106, e109, g110, i113, or L114, and wherein the IL-7A protein is not IL-7. In an aspect, the polypeptide is encoded by SEQ ID. NO.: 3. The present invention comprises a vector comprising the nucleic acid of the nucleic acid encoding an IL-7A protein having an amino acid sequence as set forth in SEQ ID. NO.: 7, wherein one or more amino acids are substituted at q36, s39, v40, v43, q47, t97, d99, L102, L105, k106, e109, g110, i113, or L114 or SEQ ID. NO.: 3. The present invention comprises host cell comprising the nucleic acid encoding an IL-7A protein having an amino acid sequence as set forth in SEQ ID. NO.: 7, wherein one or more amino acids are substituted at q36, s39, v40, v43, q47, t97, d99, L102, L105, k106, e109, g110, i113, or L114 or SEQ ID. NO.: 3. The present invention comprises a polypeptide of SEQ ID NO. 7 having one or more amino acid substitutions at sites q36, s39, v40, v43, q47, t97, d99, L102, L105, k106, e109, g110, i113, or L114.

The present invention comprises a composition comprising an isolated polypeptide having an amino acid sequence as set forth in SEQ ID. NO.: 7, wherein one or more amino acids are substituted at q36, s39, v40, v43, q47, t97, d99, L102, L105, k106, e109, g110, i113, or L114, and a pharmaceutically acceptable carrier. The polypeptide may have amino acids that are substituted with an amino acid having a different property. In aspects, the polypeptide has a mutation at site t97. In aspects, the t97 is substituted with valine.

The present invention comprises a method of treating an immunodeficiency condition in a subject, comprising, administering a therapeutically effective amount of cells to the subject, wherein the cells were contacted with an IL-7A protein prior to administration. In aspects, the immunodeficiency comprises depleted bone marrow cells. In aspects, the immunodeficiency condition is the result of radiation or chemotherapy. The present invention comprises a method of treating an immunodeficiency condition in a subject, comprising, administering a therapeutically effective amount of an IL-7A; and b) alleviating or modulating the immunodeficiency condition in the subject. In aspects, the immunodeficiency comprises depleted bone marrow cells. In aspects, the immunodeficiency condition is the result of radiation or chemotherapy.

The present invention comprises a method of inducing proliferation of immune cells in a subject in need thereof, comprising, administering a therapeutically effective amount of a composition comprising the IL-7A protein of claim 1. In aspects, the method further comprises co-administering a therapeutically effective amount of stem cells. In aspects, the stem cells are autologous or allogenic stem cells. In aspects, the stem cells have been contacted with an IL-7A protein. In aspects, the IL-7A protein has an amino acid sequence as set forth in SEQ ID. NO.: 7, wherein one or more amino acids are substituted at q36, s39, v40, v43, q47, t97, d99, L102, L105, k106, e109, g110, i113, or L114. The present invention comprises a method of increasing immune cell reconstitution following stem cell transplantation in a subject, comprising administering a composition comprising a therapeutically effective amount of an IL-7A protein to the subject. In aspects, the IL-7A protein has an amino acid sequence as set forth in SEQ ID. NO.: 7, wherein one or more amino acids are substituted at q36, s39, v40, v43, q47, t97, d99, L102, L105, k106, e109, g110, i113, or L114.

In general, when used for treatment, therapeutic compositions may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

The term "therapeutically effective" means that the amount of the composition used is of sufficient quantity to ameliorate one or more causes or symptoms of a disease or disorder, such as aberrant cell growth, tumor development, and cancer. Such amelioration only requires a reduction or alteration, not necessarily elimination. Effective dosages and schedules for administering the disclosed compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products.

The specific effective amount of a composition comprising the disclosed polypeptides or nucleic acids for any particular subject or patient will depend upon a variety of factors including the disease or disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts.

For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of ischemia-reperfusion injury, trauma, drug/toxicant induced injury, neurodegenerative disease, cancer, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular subject or patient: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

The effective amount of the disclosed composition may be given daily, every other day, weekly, monthly, bi-monthly, every other monthly, yearly, or at any other interval that is determined by the physician or provider to be effective. For example, the effective daily dose can be divided into multiple doses for purposes of administration. Consequently, single dose compositions can contain such amounts or submultiples thereof to make up the daily dose. Disclosed compositions can also be administered as part of a combination of anti-tumor or anti-cancer treatments. In an aspect, disclosed compositions can be administered to the subject or patient prior to treatment with an anti-tumor or anti-cancer treatment. In an aspect, disclosed compositions can be administered concurrently with the anti-tumor or anti-cancer treatment. In an aspect, discloseds composition can be administered subsequent to the anti-tumor or anti-cancer treatment. In an aspect, the patient or subject receives both treatments on an alternating or rotating schedule. In an aspect, the subject or patient receives a singular treatment with the disclosed composition. In an aspect, the subject or patient receives at least one treatment with the disclosed composition. In an aspect, the subject or patient receives at least one treatment with the disclosed composition and at least one other anti-tumor or anti-cancer treatment.

In a further aspect, an effective amount can be determined by preparing a series of compositions comprising varying amounts of the disclosed compositions such as the disclosed polypeptides and nucleic acids and determining the release characteristics in vivo and in vitro and matching these characteristics with specific pharmaceutical delivery needs, inter alia, subject body weight, disease condition and the like.

The dosage can be adjusted by the individual physician or the subject in the event of any counter-indications. Dosage can vary, and can be administered in one or more dose administrations daily, for one or several days. Guidance can be found in the literature for appropriate dosages for given classes of pharmaceutical products.

The terminology used herein is for the purpose of describing particular aspects only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The amino acid abbreviations used herein are conventional one letter codes for the amino acids and are expressed as follows: Ala or A for Alanine; Arg or R for Arginine; Asn or N for Asparagine; Asp or D for Aspartic acid (Aspartate); Cys or C for Cysteine; Gln or Q for Glutamine; Glu or E for Glutamic acid (Glutamate); Gly or G for Glycine; His or H for Histidine; Ile or I for Isoleucine; Leu or L for Leucine; Lys or K for Lysine; Met or M for Methionine; Phe or F for Phenylalanine; Pro or P for Proline; Ser or S for Serine; Thr or T for Threonine; Trp or W for Tryptophan; Tyr or Y for Tyrosine; Val or V for Valine; Asx or B for Aspartic acid or Asparagine; and Glx or Z for Glutamine or Glutamic acid.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

As used herein, "cognate" refers to an entity of a same or a similar nature.

As used herein, the term "amino acid sequence" refers to a list of abbreviations, letters, characters or words representing amino acid residues.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One aspect of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof As used herein, "reverse analog" or "reverse sequence" refers to a peptide having the reverse amino acid sequence as another reference peptide. For example, if one peptide has the amino acid sequence ABCDE, its reverse analog or a peptide having its reverse sequence is as follows: EDCBA.

"Inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100 percent, or more, or any amount of promotion in between compared to native or control levels. In an aspect, the increase or promotion is 10-20, 20-30, 30-40, 40-50, 50-60, 60-70, 70-80, 80-90, or 90-100 percent as compared to native or control levels. In an aspect, the increase or promotion is 0-25, 25-50, 50-75, or 75-100 percent, or more, such as 200, 300, 500, or 1000 percent more as compared to native or control levels. In an aspect, the increase or promotion can be greater than 100 percent as compared to native or control levels, such as 100, 150, 200, 250, 300, 350, 400, 450, 500 percent or more as compared to the native or control levels.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The term "sample" can refer to a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid). A sample may also be any body fluid or excretion (for example, but not limited to, blood, urine, stool, saliva, tears, bile) that contains cells or cell components.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

It should be kept in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding of the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

EXAMPLES

The Examples below present data showing that high doses of the native form of IL-7 have negative consequences upon the immune system and also demonstrate the feasibility of producing an attenuated form of IL-7 (IL-AT) by inducing a single point mutation.

Example 1

IL-7 Dose Responsiveness Shown in a T-Cell Line

The need for IL-7 to support T-cell growth was examined using an IL-7 dependent T-cell line, D1 (CD4$^-$CD8$^-$) (Kim et al., 2003). D1 cells grow best at the IL-7 dose of 50 ng/ml (FIGS. 1A, 1B). Decreasing the IL-7 dose to 10 ng/ml still supports survival (94% viable) but proliferation is decreased (15% DNA synthesis) (FIGS. 1A and 1B). IL-7, at concentrations at 2 ng/ml or less, fail to support D1 cells. These results were confirmed by examining phosphorylated STAT5, a direct indicator of the strength of the IL-7 signal. At IL-7 doses of 50 and 10 ng/ml, we detected a significant number of D1 cells with elevated levels of phospho-STAT5, 56% and 35% respectively (FIG. 1C). The conclusion drawn from these results is that a high dose of IL-7 (50 ng/ml) supported both survival and proliferation that is dependent upon STAT5 signaling; while a lower dose of IL-7 (10 ng/ml) can still promote survival in a STAT5-dependent manner.

Example 2

High Dose IL-7 Negatively Impacts Upon CD4 T-Cell Growth

Figure 2:
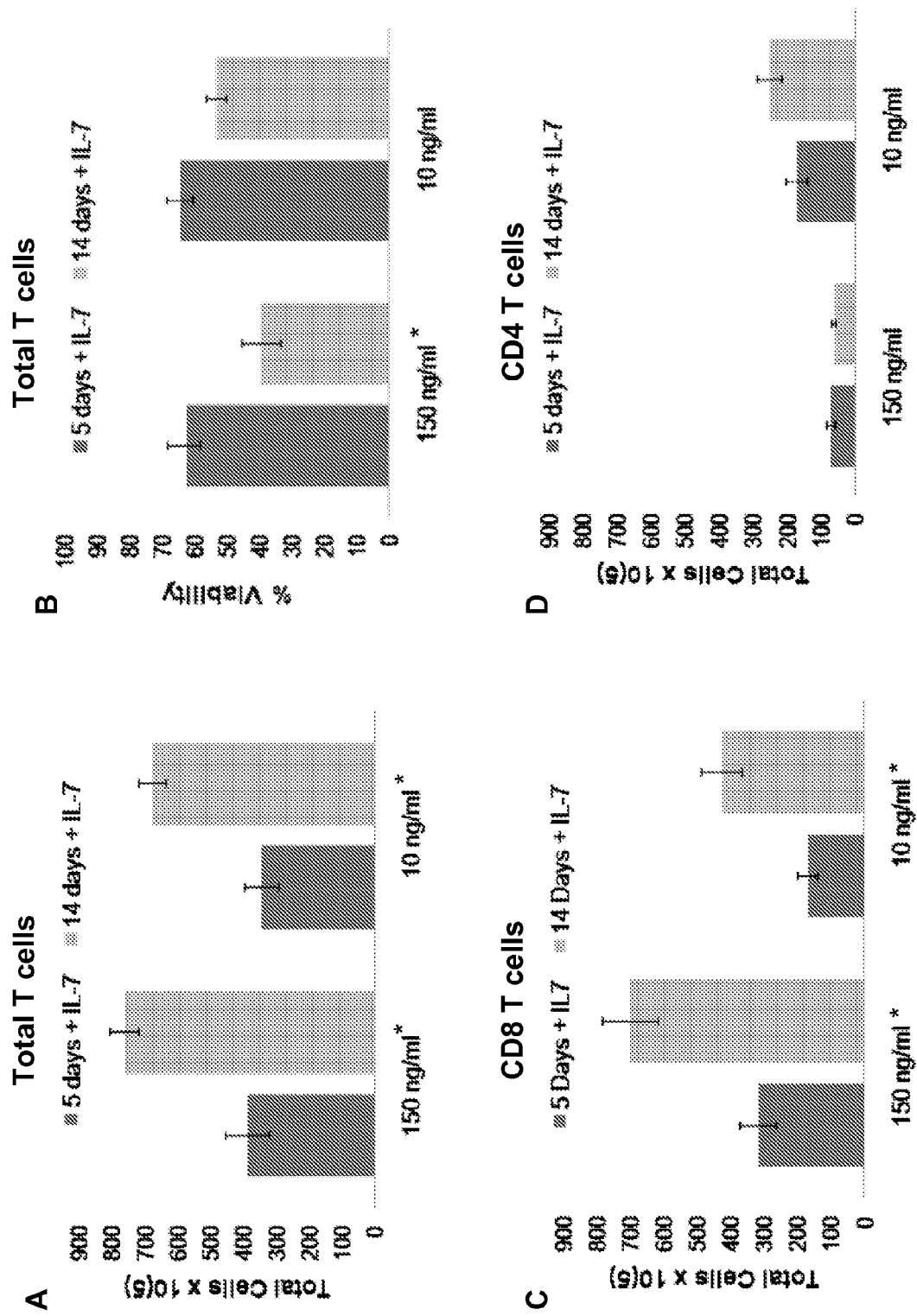
FIG. 2A-E are graphs and plots showing that high dose IL-7 impairs the growth of CD4 T-cells.
Figure 2:
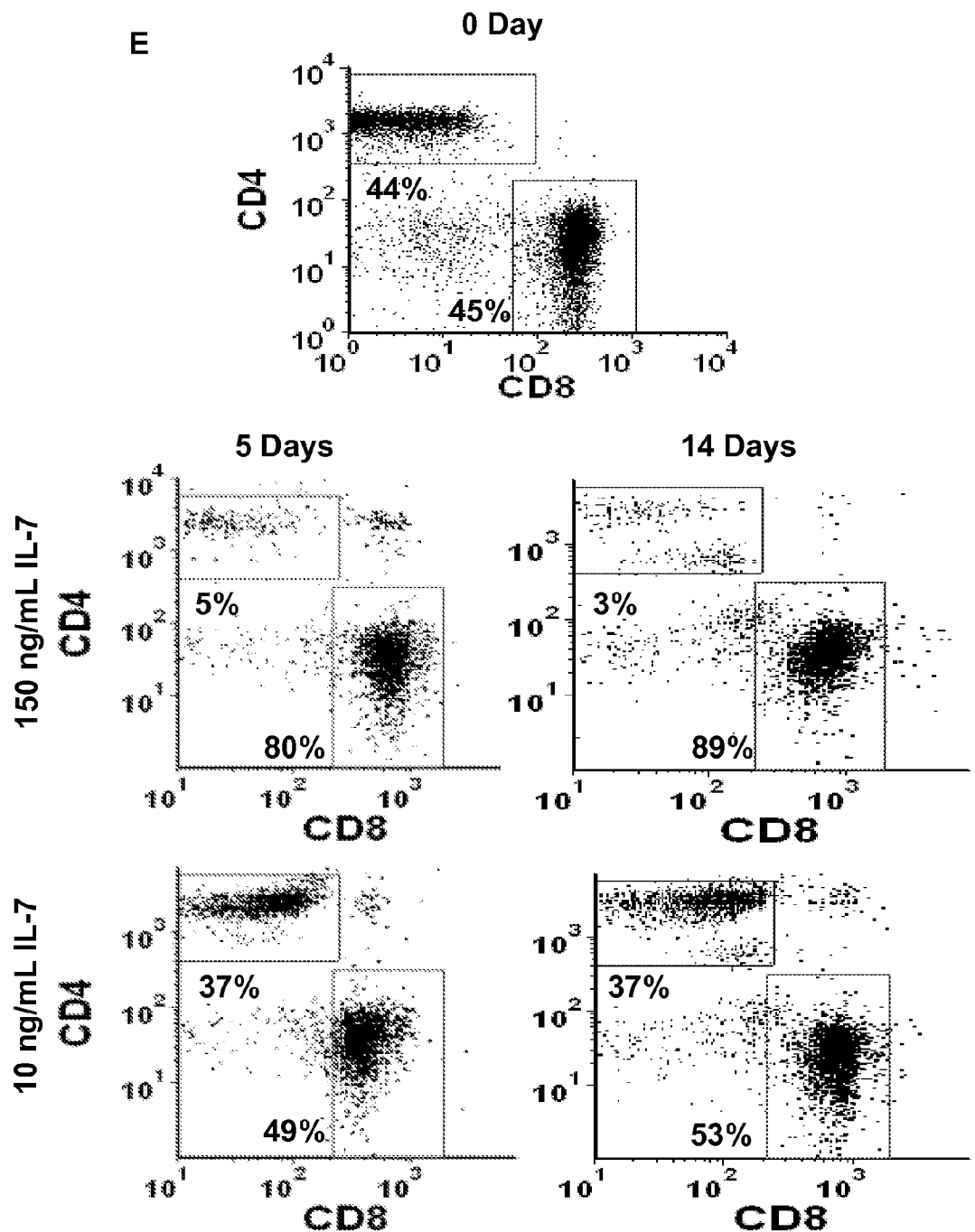

To examine the activity of IL-7 on primary T-cells, lymph node cells from C57B1/6 mice were isolated and cultured with IL-7 for 0-14 days at high (150 ng/ml) and low (10 ng/ml) concentration. Lymph node cells were isolated from C57B1/6 mice and cultured with IL-7 for 0, 5 and 14 days at high (150 ng/ml) and low (10 ng/ml) concentrations. T-cells were counted and viability determined by FSC/SSC gating using an Accuri C6 flow cytometer. (FIGS. 2A-D). T-cells were incubated with saturating amounts of anti-CD4-PE and anti-CD8-PerCP antibodies and assayed by flow cytometry (FIG. 2E). Analysis was performed with FSC Express. The results in FIG. 2 indicated that high dose IL-7 preferentially supported the expansion of CD8 T-cells at the expense of CD4 T-cells (FIGS. 2B-D). This was seen in FIG. 2E showing a notable loss of CD4 T-cells after culture for 14 days with high dose IL-7. However, by culturing the lymph nodes cells with low dose IL-7 (10 ng/ml) growth and viability of all T-cells were supported (FIG. 2A, B)—specifically CD4 T-cells as well as CD8 T-cells (FIG. 2C-D). This showed that supraphysiological doses of IL-7 resulted in suboptimal reconstitution of lymphocytes with severe depletions in the CD4 T-cell populations.

The results in FIG. 2 indicated that high dose IL-7 (150 ng/ml) supported the growth of T-cells through the 14 days of culture, although viability decreased over time (FIG. 2A). It was discovered that the reason for the harmful effect of high dose IL-7 upon CD4 T-cells was due to the inhibitory activity of the Src kinase, LCK. In these cells, LCK was interacting with the JAK/STAT pathway to optimize the IL-7 signal at a lower dose (Kittipatarin et al., 2010b). These results demonstrated the detrimental effect of high dose IL-7 upon the expansion of CD4 T-cells. The implications were that the supraphysiological doses of IL-7 resulted in suboptimal reconstitution of lymphocytes with severe depletions in the CD4 T-cell populations. In Example 8 below, the ability of IL-7 ligand to restore and sustain a normal, balanced repertoire of T-cells was examined.

Example 3

High Dose IL-7 Drives Proliferation but Inhibits Lymphocyte Movement

It was found that high dose IL-7 promoted the proliferation T-cells (as shown in FIG. 1) through the activity of the phosphatase, Cdc25A (Khaled et al., 2005). Cdc25A is a potent transducer of IL-7 growth signals to CD8 T-cells (Kittipatarin et al., 2010a), specifically under the high dose conditions as shown in FIG. 2. Mice were injected with 10 μg of IL-7, 100 μg of an anti-IL-7 neutralizing antibody (M25) or a mixture of the two and sacrificed after 3 days for analysis. Lymph nodes were excised, photographed and total cell counts determined using the Accuri C6 flow cytometer. See FIG. 3A-C. In mice injected with IL-7, it was observed that, within 3 days of a single IL-7 injection (10 μg), lymph nodes were recovered that were severely depleted of lymphocytes (FIG. 3A). In contrast, spleens from these mice did not display similar effects. When IL-7 was pretreated with a neutralizing antibody (M25) prior to injection, greater numbers of lymphocytes in lymph nodes were recovered as compared to control mice (FIG. 3A). These results suggested that a strong IL-7 signal negatively affected lymphocyte movement. To explain this, it was noted that treatment with high dose IL-7 (that drives proliferation) also caused down regulation of the adhesion molecule, CD62L, which directs T-cells to lymph nodes (FIG. 3B). Murine T-cells were cultured for 14 days with 150 or 10 ng/ml IL-7 and examined for CD44 and CD62L using FITC or PE conjugated antibodies by flow cytometry. Low dose IL-7 (which supports survival) did not cause decreased CD62L expression (FIG. 3B). Time-lapse microscopy was used to track the movement of enriched CD62Llo or CD62Lhi murine T-cells treated with vehicle (DMSO) or with the CD62L ligand, PSGL-1 (FIG. 3C). Images were obtained using the UltraView (PerkinElmer) spinning disc confocal system. Velocity was determined using Volocity software (PerkinElmer). The movement of CD62Lhi cells, but not CD62Llo cells, was arrested by the CD62L ligand, PSGL-1, mimicking the trafficking of CD62Lhi cells to lymph nodes. Upon inhibition of Cdc25A, movement of CD62Llo cells was arrested in response to PSGL-1 (FIG. 3C). These results suggested that high circulating levels of IL-7, that promotes Cdc25A-driven proliferation, would impair trafficking of T-cells to lymph nodes.

It was discovered that the dephosphorylating activity of Cdc25A induced cyclin dependent kinases (Cdks) that phosphorylated the transcription factor, Foxol, responsible for inducing the expression of CD62L, retaining it in the cytosol. Hence, high dose IL-7 would activate Cdc25A and prevent the nuclear translocation of Foxol, down regulating the expression of CD62L (Kittipatarin et al., 2010a). It was observed that the movement of $CD62L^{hi}$ cells, but not $CD62L^{lo}$ cells, was arrested by the CD62L ligand, PSGL-1 mimicking the trafficking of $CD62L^{hi}$ cells to lymph nodes. Upon inhibition of Cdc25A, movement of $CD62L^{lo}$ cells was now arrested in response to PSGL-1 (FIG. 3C). These results suggested that high circulating levels of IL-7, that promoted Cdc25A-driven proliferation, impaired trafficking of T-cells to lymph nodes. It is within lymph nodes that naïve T-cells become antigen-activated.

Example 4

Attenuating the IL-7 Signal

Figure 3:
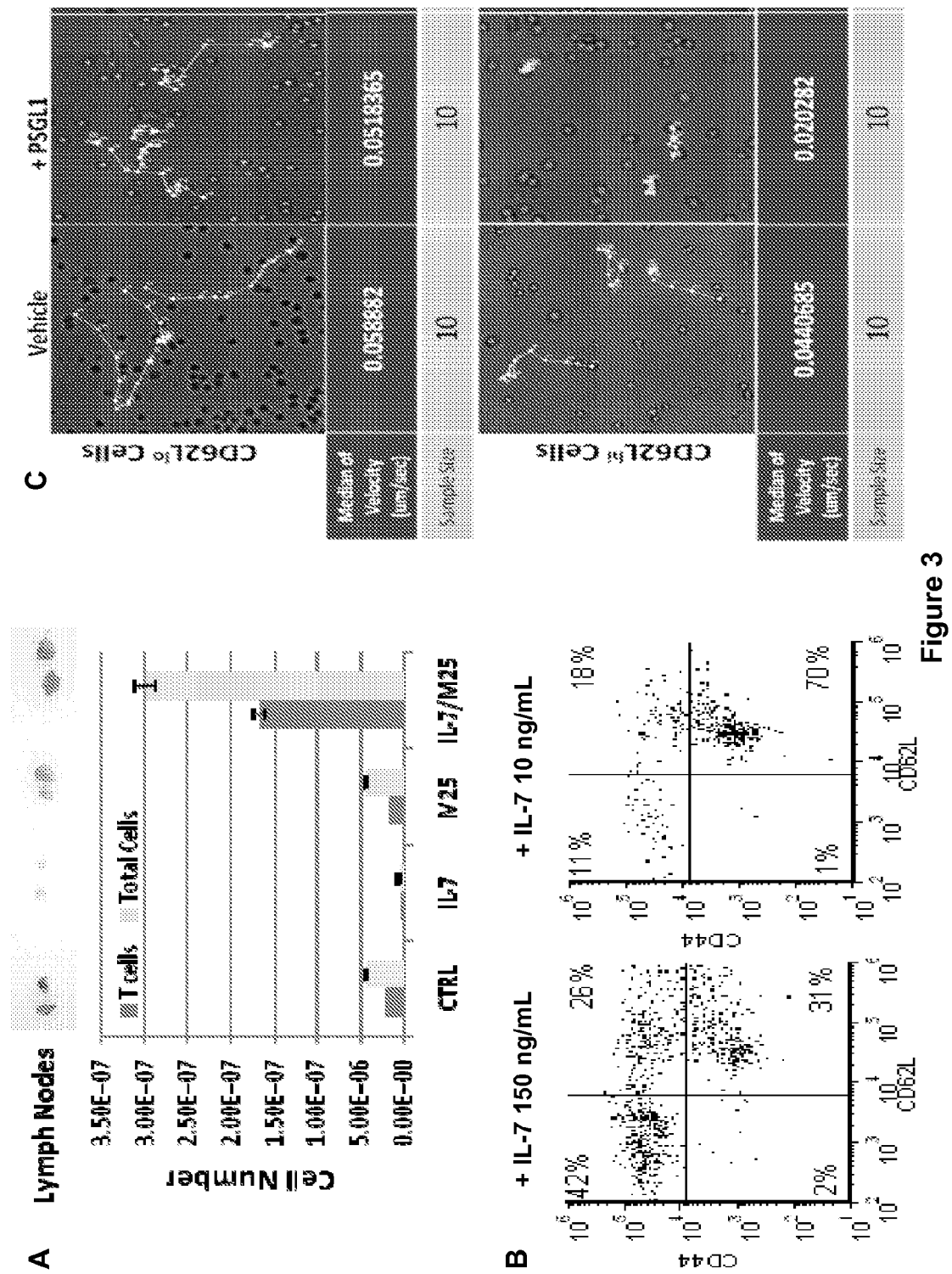
FIG. 3A-C are graphs and micrographs that show high dose IL-7 down-regulates CD62L, impairing lymphocyte movement.
Figures 4A, 4B:
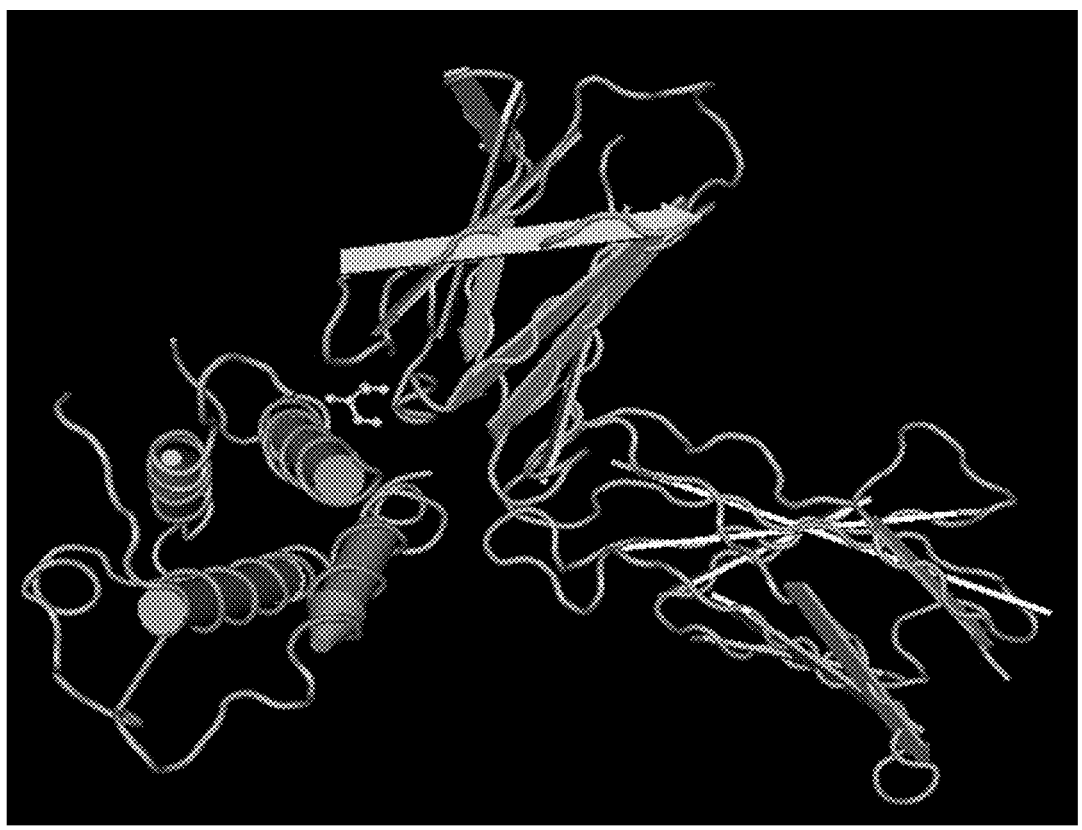
FIGS. 4A and B show a schematic and chart of an attenuated IL-7 (IL-7A).

The data in the FIGS. 1-3 suggested that a strong IL-7 signal could have negative impact on T-cell growth and trafficking. Weakening the binding of IL-7 to its receptor would reduce the strength of the signal delivered to the receptor and prevent the negative effects described. To achieve this, the structure of IL-7 (green) was examined to identify residues required for the interaction with the IL-7 receptor (yellow). See FIG. 4A. There were fourteen residues on IL-7 that interact with corresponding residues on the IL-7 receptor—see table on the right. This goal was not to inhibit but rather to attenuate binding—mutating Thr97 on IL-7 that was part of the hinge region that enabled binding to the receptor was chosen. Mutation of Thr97 reduced the flexibility of IL-7 and altered the conformation required for IL-7 to bind to the receptor. Mutation of Thr97 did not directly interfere with direct binding to the receptor. The end result was attenuated binding to the receptor. Other sites adjacent to Thr97, shown in the table, (FIG. 4B) would potentially impede the binding of IL-7 to the IL-7R to a greater extent.

Example 5

Creating an IL-7A

1. Generation of Hmm-IL-7AT plasmid. In order to express IL-7AT in a mammalian system, first, site directed mutagenesis was performed to mutate the Threonine at position 97 to a Valine—see underlined in sequence in FIG. 5. Mutation was generated with the QuickChange II Site Directed Mutagenesis kit (Strategene). The mutated IL-7AT cDNA was then amplified using a forward primer containing an HMM sequence: (ATG TGG TGG CGC CTG TGG TGG CTG CTG CTG CTG CTG CTG CTG CTG TGG CCC ATG GTG TGG GCC). The fusion protein was flanked by 5' EcoRI and 3' XhoI restriction sequences to allow for cloning into pcDNA6/His B vector for expression in mammalian system (Invitrogen). Sequencing was done to ensure proper orientation of the cDNA, retention of the mutation, and that the ATG start codon was on the HMM sequence to allow for accurate transcription.

Figure 6:
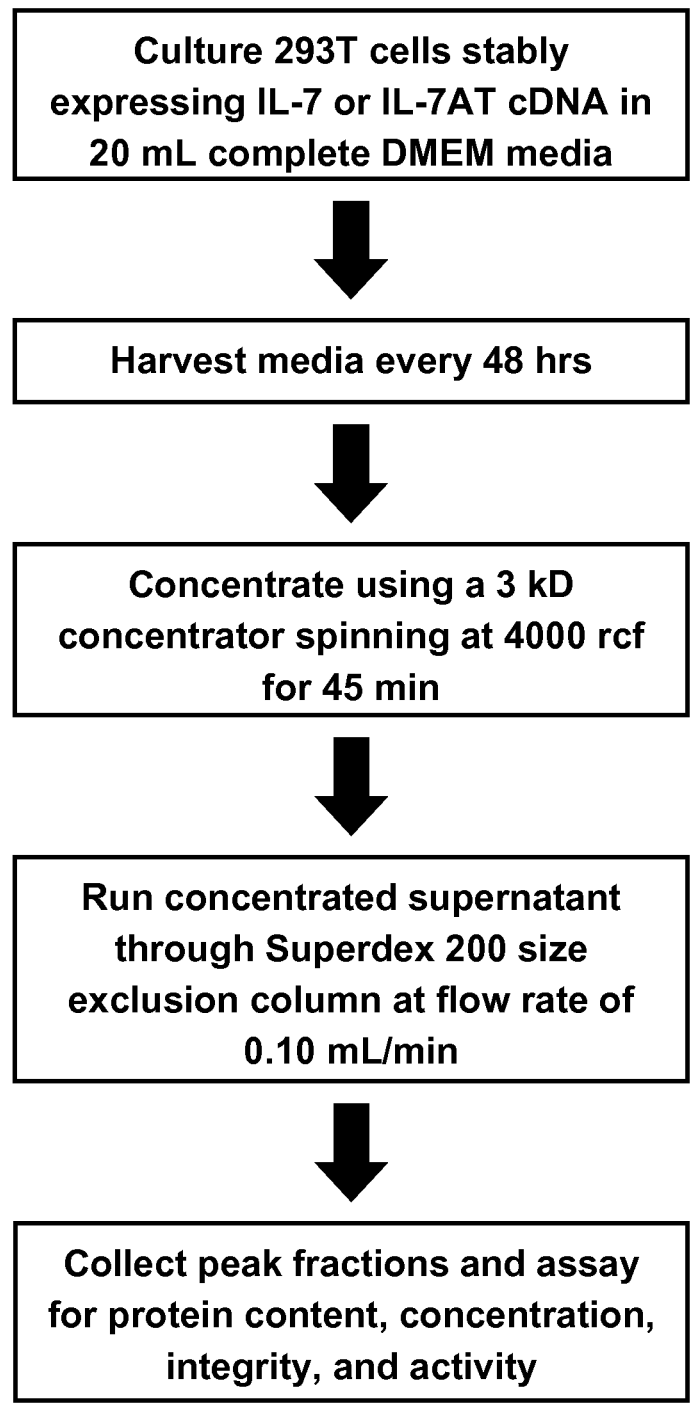
FIG. 6 shows a schematic of production of IL-7AT.

2. Production of IL-7AT. The expression vector used for human IL-7 (hIL-7) expression was pORF9-hIL-7, in which site-directed mutagenesis was performed to convert Thr97 to Val97 and produce IL-7AT. The cDNAs for IL-7WT and IL-7AT were modified to include the sequence for the HMM secretion signal peptide, MWWR-LWWLLLLLLLWPMVWA, and then was cloned into a pcDNA6/HisB mammalian expression vector. The HMM-IL-7AT vector was transfected at a concentration of 1 ug/ul into the Human Embrionic Kidney (HEK) 293T cell line according to the manufacturer's protocol using the Mirus LT-1 transfection kit. Cells were transfected in 6 well plates and then subjected to blasticidin treatment for 2 weeks to select for stably-expressing cells. The cells were grown in Delbucco's Modified Eagles Medium (DMEM, Cellgro) supplemented with 10% FBS (Hyclone) and 1% Penicillin/Streptomycin. Initial production was scaled up to T75 flasks. Following the protocol shown in FIG. 6, fractions were collected and protein concentration determined by measuring optical density (OD) at 280. Average yields of cytokine were 0.6-0.8 mg/mL. Fractions were assayed by FT/IR to determine structural integrity, western blot for purity, and were tested in vitro for biological activity.

Figure 7:
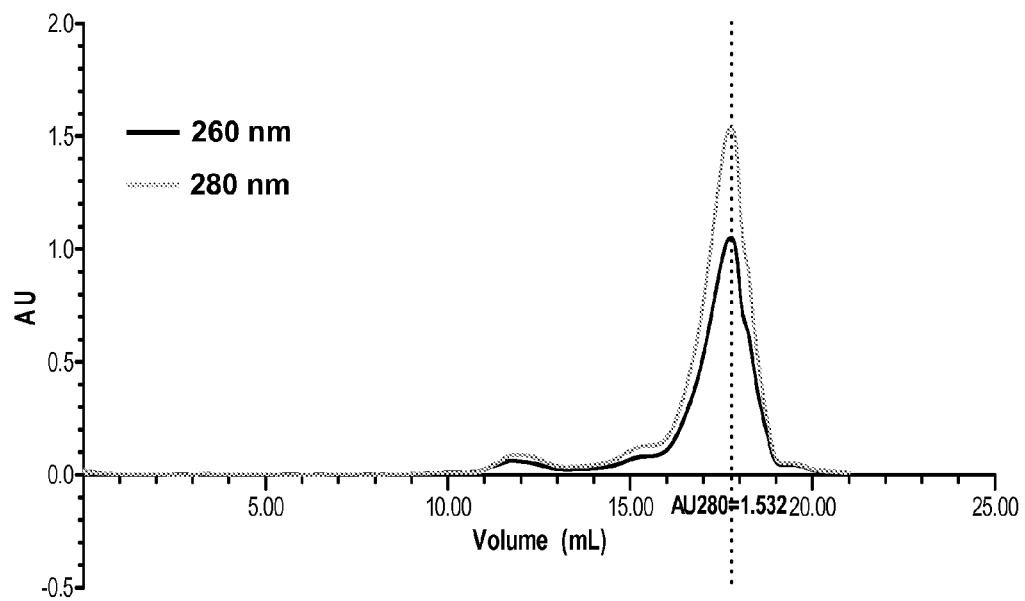
FIG. 7 is a graph that shows harvesting and purification of IL-7AT.

3. Harvesting and Purification of IL-7AT. The HMM protein sequence allowed for secretion of the protein into the media. Media was collected at 48 hour increments, and each 20 mL collected volume was concentrated down to 2 mLs by centrifugation (Eppendorf) at 4000 rpm for 45 min through a 3,000 dalton (da) concentrator (Millipore). The concentrated media was loaded in 1 mL increments onto a Superdex 200 size exclusion column (GE). The column was attached to a BioLogic DuoFlow Fast Protein Liquid Chromatography (FPLC) machine (BioRad) and the sample was run through the column at a flow rate of 10 uL/min to allow for maximum resolution of peak fractions. The running buffer was a Hepes Buffer (20 mM Hepes, 120 mM NaCl, 50 mM L-Arginine, 50 mM L-Glutamic Acid), using potassium hydroxide (KOH) to achieve a pH of 7.2. (A) Based on the size of IL-7AT (20.187 kD) and the specifications of the Superdex 200 column, the predicted elution volume of a protein of this size is at ~17 mLs. Based on a representative chromatograph of the absorbance units (AU) at 280 nm and 260 nm, the peak absorbance occurs at 17.7 mLs. The entire 17th mL, as well as the flanking volumes were collected to assay for protein concentration by OD 280 and the concentration was determined to be ~0.65 mg/mL. (B) Presence of the target protein (22 kD) was verified by western blot using the primary antibody, M25 (Amgen). See FIG. 7.

Example 6

IL-7AT Displays Decreased Binding to the IL-7R

Figure 8:
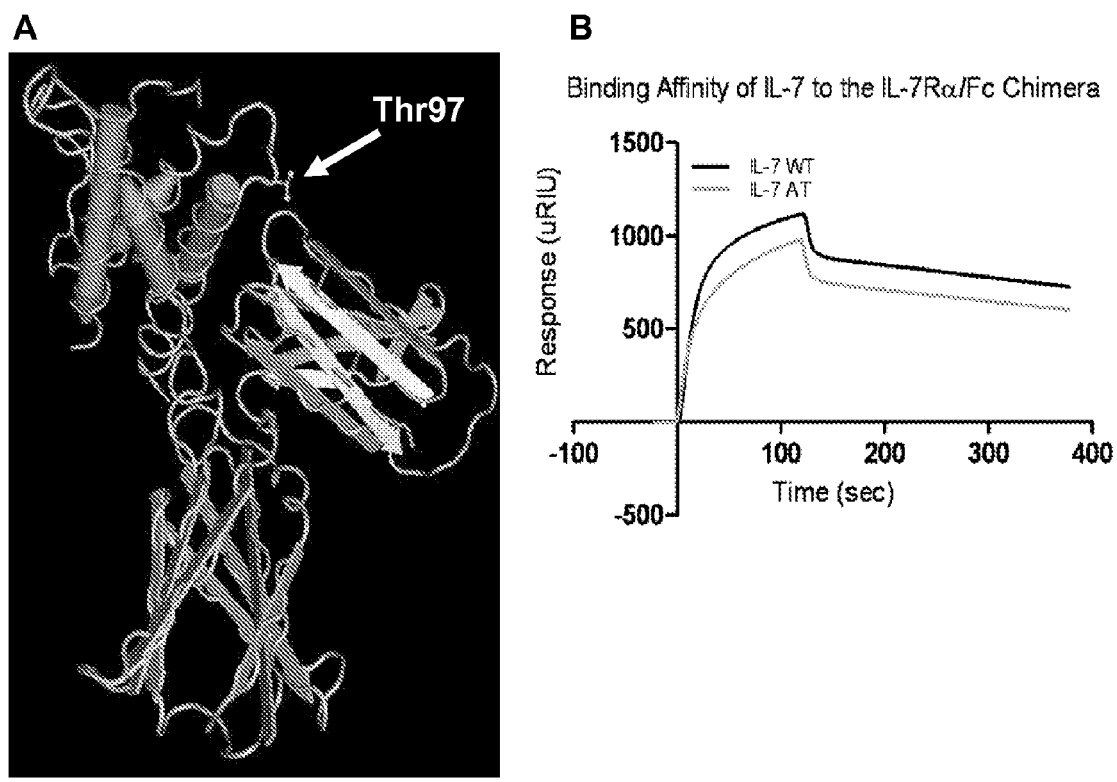
FIG. 8A shows the structure of IL-7AT and B is a graph that shows IL-7AT displays decreased binding to the IL-7R.
Figure 9:
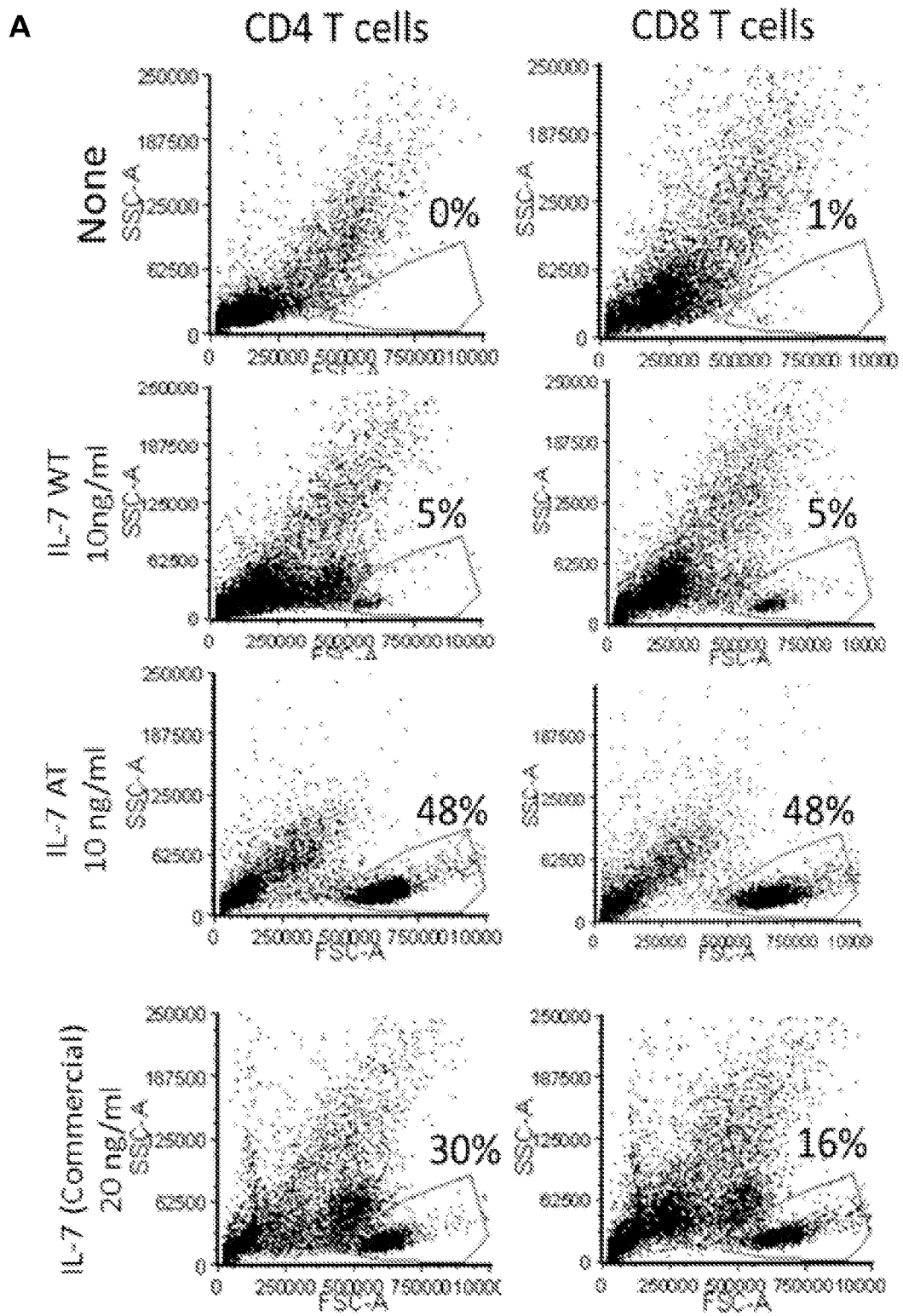
FIG. 9A-C are graphs showing that T cell subset growth was balanced through an attenuated signal.
Figure 9:
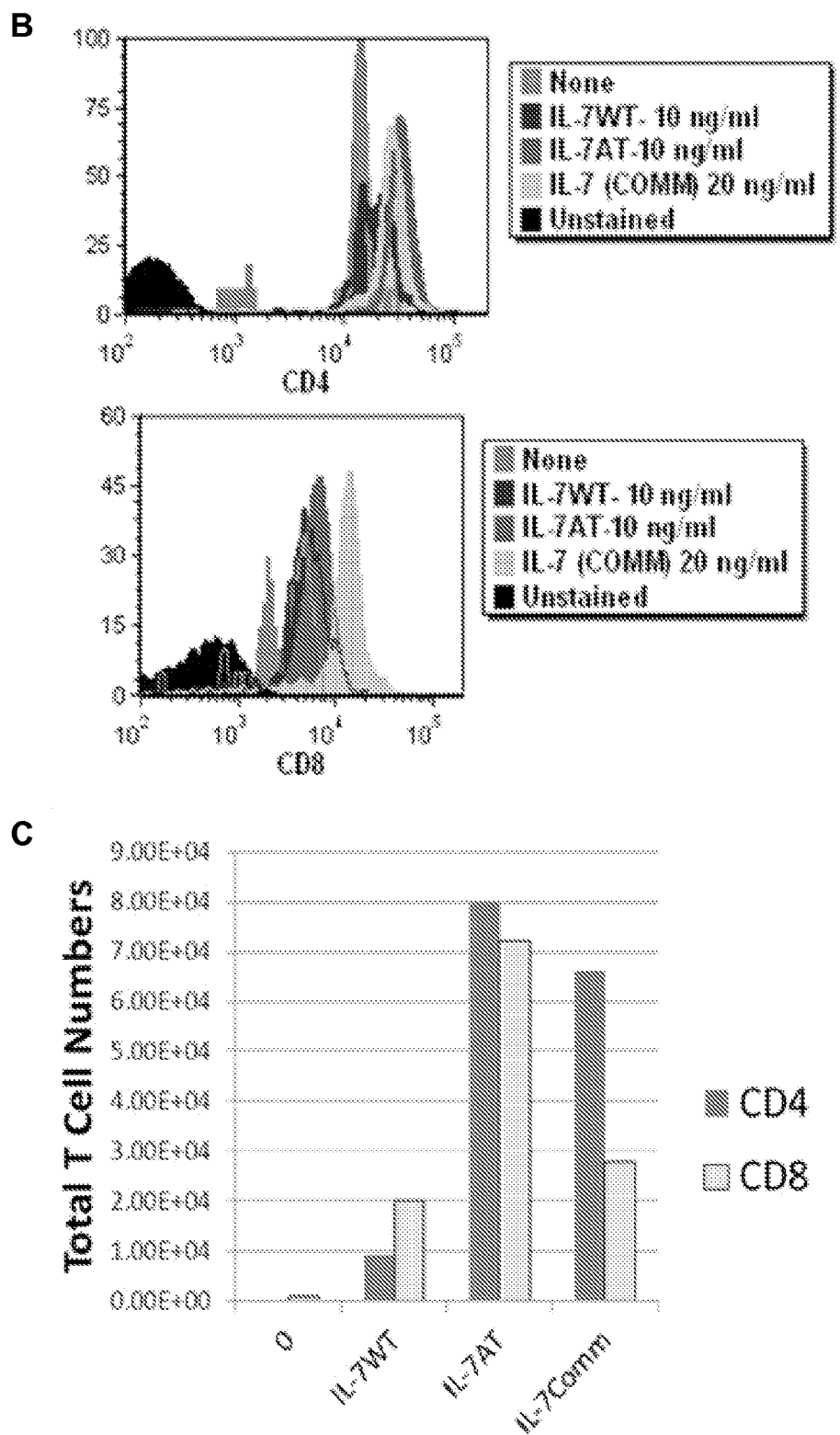
Figure 10A:
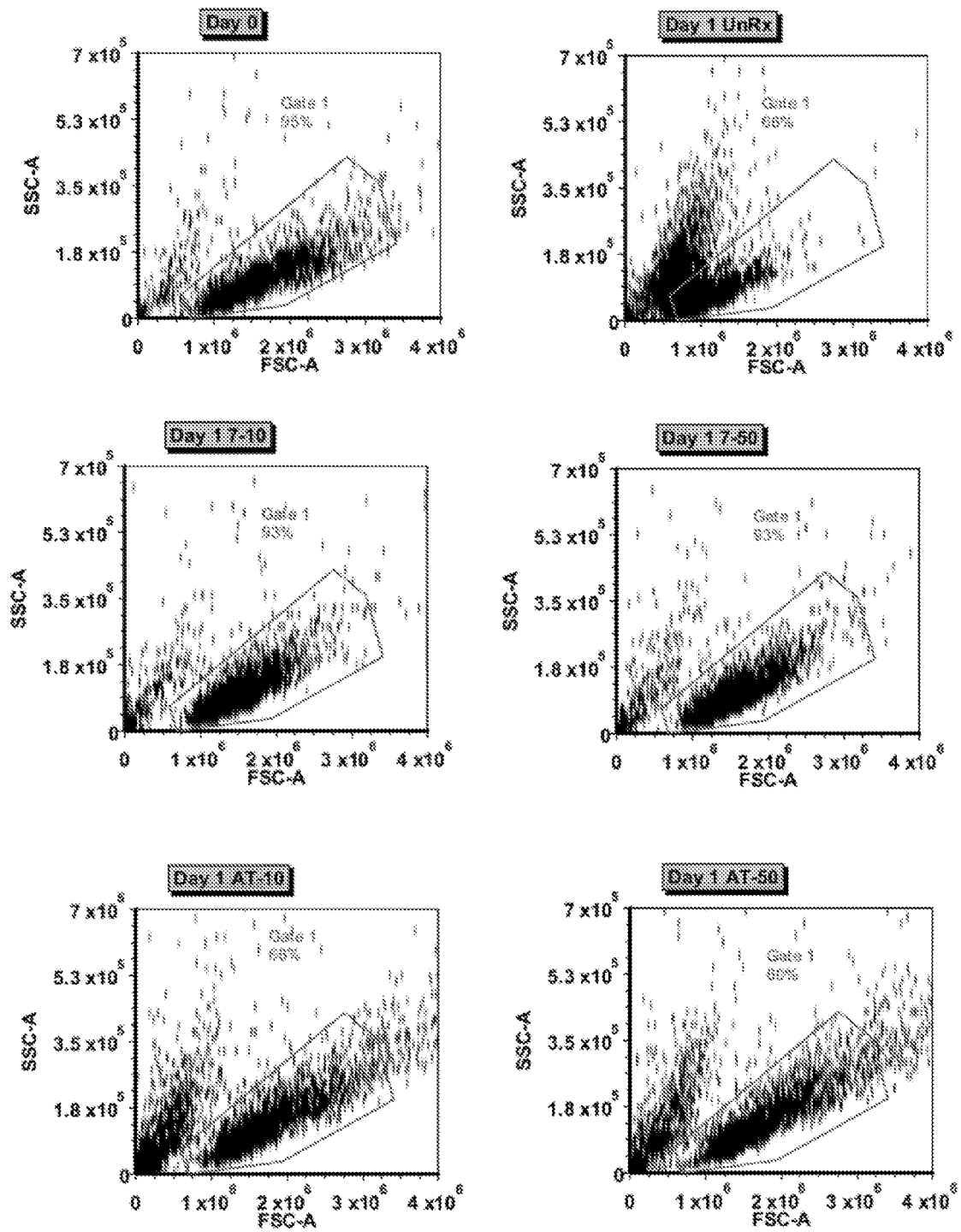
FIG. 10A-C are graphs showing that an attenuated signal that supported survival.
Figure 10B:
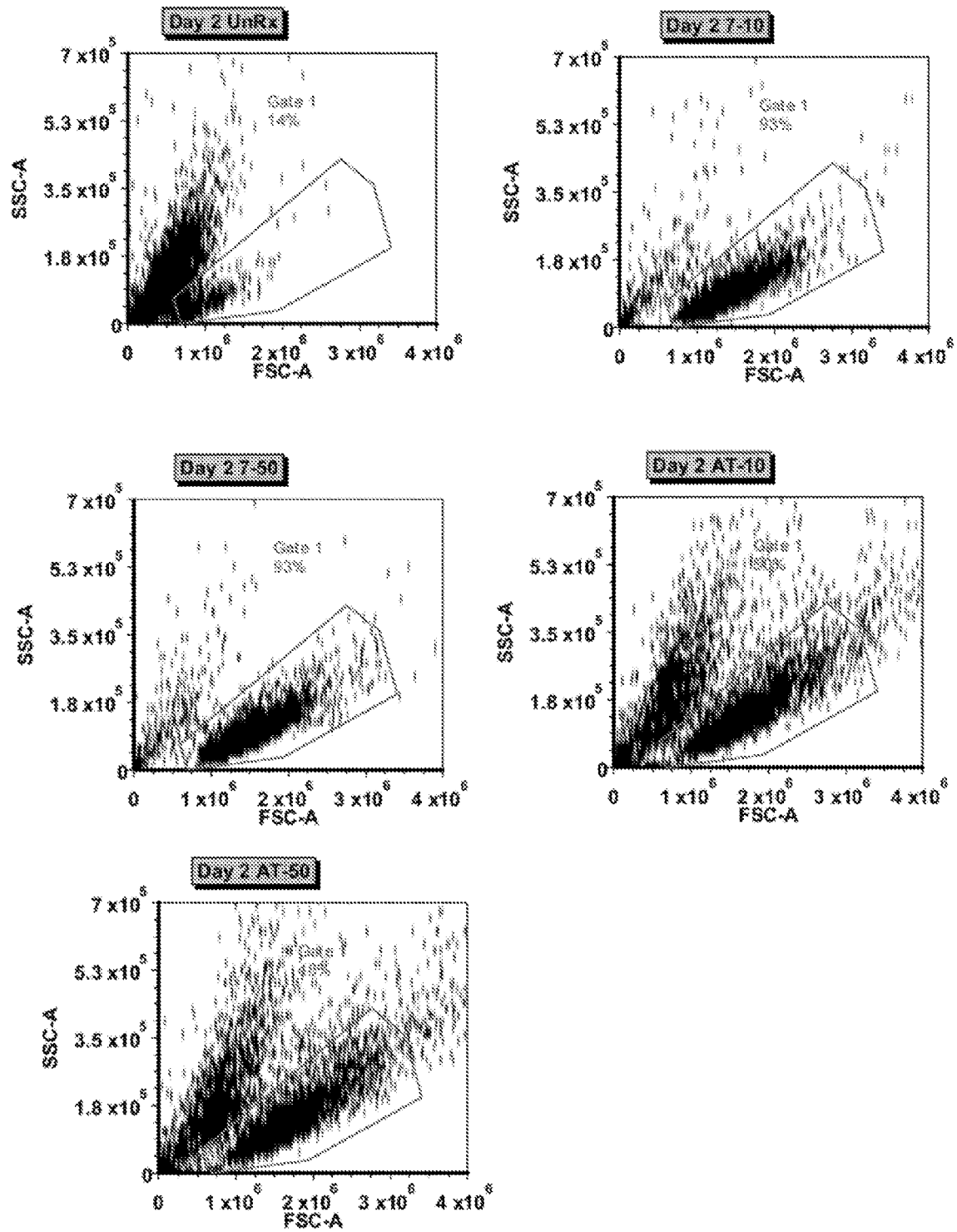
Figure 10C:
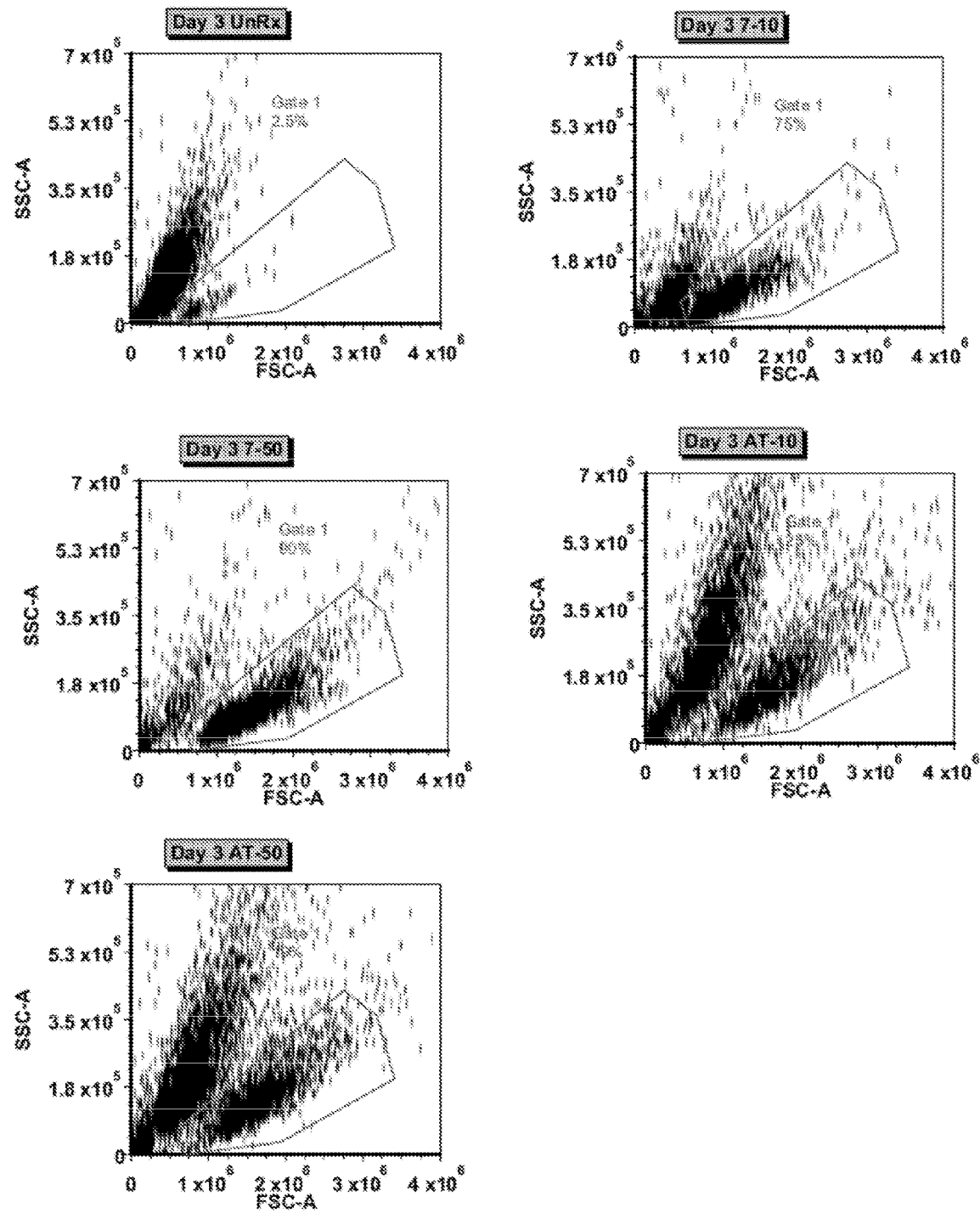

To engineer IL-7AT, the structure of IL-7 (green, FIG. 8A) upon binding to the IL-7 receptor (IL-7R) (beige, FIG. 8A). The in silico analysis revealed that Thr97 (highlighted in yellow) is located at a turn near the helix which directly interacts with IL-7R. Thr97 is located within a site that confers flexibility. To produce IL-7AT, Thr97 was mutated to Val and the protein expressed and purified. Binding to an IL-7R/

Fc fusion protein was determined by surface plasmon resonance (SPR). Association (Ka), Dissociation (Kd) and total binding constant (KD) were calculated using the Scrubber2 program (BioLogic Software). IL-7AT had reduced response to IL-7R (decrease of 1500 units) as compared to the native form of IL-7 (FIG. 8B) and Table below, while, once bound, the total binding affinity (KD) did not change. Having the same binding affinity indicated that, at equilibrium, the ratio of free vs. bound forms was equivalent. The change in the response was due to different amounts of immobilized ligand, since the same IL-7R loaded chip was used and saturation was reached. The Ka and Kd values indicate the 1:1 binding ratio of the protein to the receptor. The change in response was the result of an alteration in the structure of IL7-AT/IL-7R complex that changed the Stokes radius and the refractive index (and resonant angle). This finding is consistent with the mutation of Thr97 decreasing the accessibility of IL-7AT to the IL-7R. These results demonstrated that we produced an attenuated form of IL-7.

Figure 11:
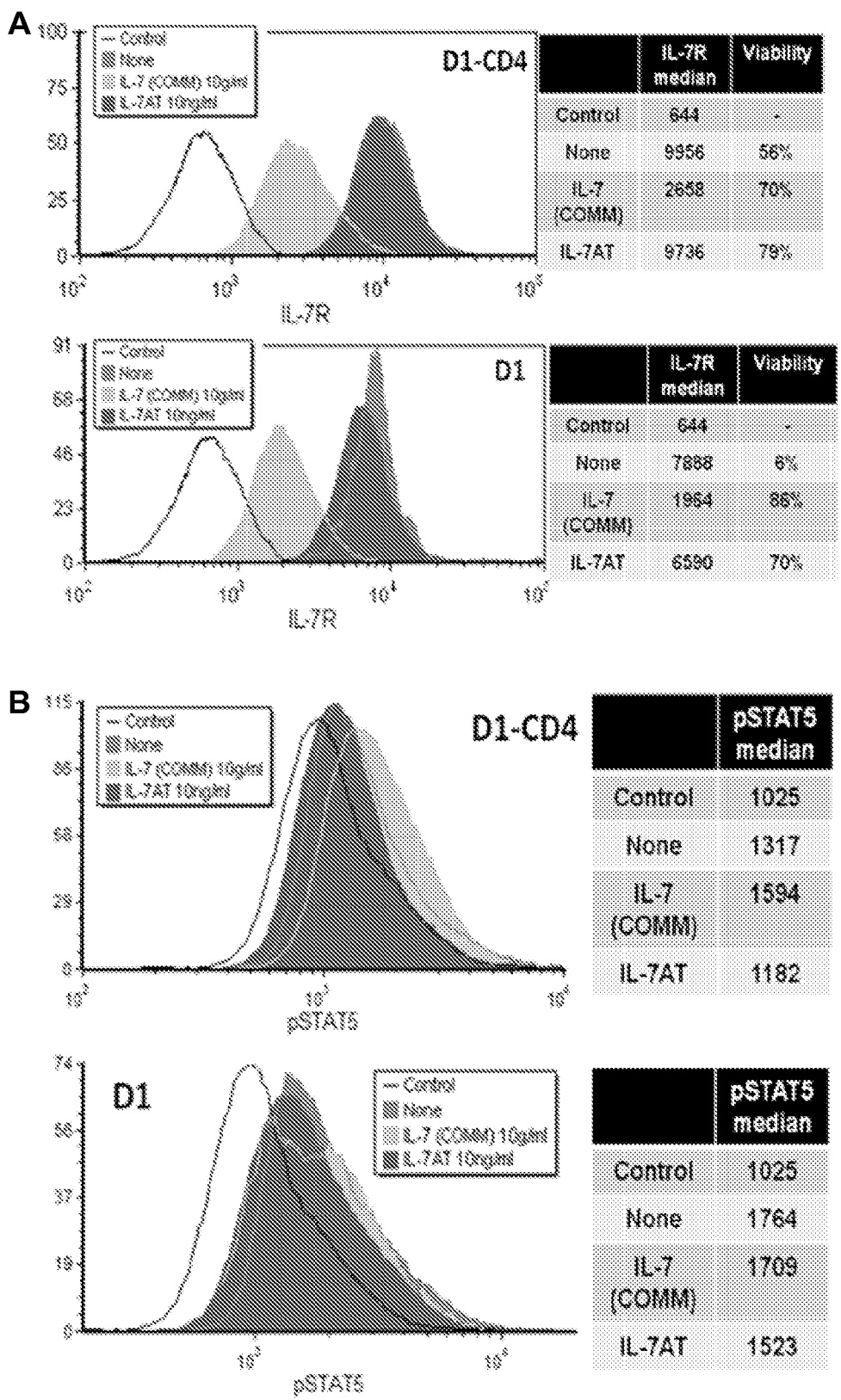
FIG. 11A-B are graphs showing that an attenuated signal maintains IL-7R levels.

| | Response (corrected) | $K_a$ | $K_d$ | $K_D$ |
|---|---|---|---|---|
| IL-7 | 8500 | 13342.2 | $1.334 \times 10^{-3}$ | 100 nm |
| IL-7 AT | 7000 | 14615.1 | $1.462 \times 10^{-3}$ | 100 nm |

As shown in FIG. 1A, D1 cells were optimally grown in 50 ng/ml of native IL-7, while D1-CD4 preferred 10 ng/ml (Kittipatarin et al., 20106). D1 and D1-CD4 were cultured with a dose range of IL-7 ligand (and IL-7 as control) from 0-150 ng/ml for 0-14 days and, at regular intervals, the levels of intracellular phospho-STAT5 were measured as an indicator of the strength of the IL-7 signal transduced through the IL-7R, as well as the levels of the IL-7R receptor itself (CD127), by flow cytometry (FACSCanto, BD Biosciences), using specific fluorescence-conjugated antibodies (BDBiosciences). To evaluate short-term effects, these experiments were performed after short 20 minute pulses with the cytokines.

Viability (Sytox staining, Molecular Probes), apoptosis (FITC-Annexin V staining, BDBiosciences) and proliferation (Click-iT® EdU Alexa Fluor® 488 Flow Cytometry Assay Kit, Invitrogen) are assessed at regular intervals with cells cultured 0-14 days with doses of IL-7 ligand (or IL-7). To examine protein levels of the anti-apoptotic proteins, BCL-2, BCL-XL or MCL-1, whole-cell as well as cytosolic and mitochondrial protein lysates are prepared from cells treated with IL-7 ligand (or IL-7). Lysates were analyzed by SDS-PAGE and immunoblotting performed with specific antibodies (anti-BCL-2, anti-BCL-XL or anti-MCL-1, Cell Signaling Tech.). Control proteins, p38 MAPK (cytosolic content), Prohibitin (mitochondrial content) and Actin (protein loading) are detected. To quantitate protein expression, the Odyssey Infared Imaging System (Li-Cor) is used with matched IRDye secondary antibodies. To assess changes in gene expression induced by IL-7 ligand (or IL-7 as control) quantitative real time PCR (qPCR) is performed with commercially available primers (Amgen) for BCL-2, BCL-XL or MCL-1, using protocols optimized for D1 and D1-CD4 cells (Chehtane and Khaled, 2010). The Fast SYBR® Green Mix (Applied Biosystems) are used with a 7500 Real-time PCR system (Applied Biosystems). β-actin is measured as an endogenous control. Relative expression is calculated for each gene by the 2-ΔΔCt method. Treatment with 50 ng/ml of IL-7 ligand promotes the viability of D1 and D1-CD4 cells but not proliferation (as compared to native IL-7 that induced both) and that, as part of the survival pathway, the anti-apoptotic proteins, BCL-2 and MCL-1 (and to lesser extent BCL-XL) are induced. Additionally, the activity of pro-apoptotic proteins like BAX or BAD is examined to show that they are repressed by IL-7 ligand.

Attenuated signal delivered by ligand correlated with reduced binding to the IL-7R (binding kinetics established by SPR) and decreased amounts of phospho-STAT5 were detected. IL-7 ligand did not cause the down-regulation of the IL-7R as has been shown to occur with the stronger signal delivered by the native cytokine (Park et al., 2004). Further, the attenuated ligand signal did not drive the proliferation of IL-7R-expressing D1 or D1-CD4 cells but rather supported their viability. This is demonstrated by induction of anti-apoptotic proteins, such as BCL-2 or MCL-1. These findings supported the use of an attenuated IL-7 signal to pre-treat stem cells for transplant, improving the quality of the immune reconstitution without causing GVHD.

Example 7

IL-7AT Supported Balanced T Cell Subset Growth Through an Attenuated Signal

As shown in FIG. 9A-C, results revealed that a single dose of IL-7AT (10 ng/ml), as compared to wild type (WT) IL-7 or commercially available (COMM) IL-7 (Peprotech), was able to sustain 48% of cells placed in cultured for 5 days (FIG. 9A). These results were significantly better than those achieved with IL-7WT or the commercial IL-7 product (FIG. 9A). Primary T cells normally die within 24 hours when cultured in standard medium (FIG. 9C); when cultured with IL-7, T-cells grow until an IL-7-sensitive population (like CD8 T cells under high dose conditions) dominates (Kittipatarin et al., 2009). Unlike the native IL-7, we found that IL-7AT produced balanced maintenance of both CD4 and CD8 T cell subsets; viability and surface staining for CD4 or CD8 showed that viable cells maintained expression of the co-receptors after 5 days in culture (FIGS. 9B, 9C).

Example 8

IL-7AT Delivered an Attenuated Signal the Supports Survival

As shown in FIG. 10A-C, IL-7AT delivered an attenuated signal that supports survival. To demonstrate that IL-7AT was providing an attenuated signal, we examined the viability of D1 cells cultured with IL-7AT or IL-7 at 10 and 50 ng/ml for 3 days, as show in progression in FIG. 10A (day 1), FIG 10B, (day 2), and FIG 10C (day 3). Viability was determined by measuring cell size (forward scatter (FSC) and granularity (side scatter (SSC)) by flow cytometry. IL-7AT did not support viability of D1 cells as effectively as the native IL-7, indicating that it was delivering an attenuated signal.

Example 9

IL-7AT Delivered an Attenuated Signal That Maintains IL-7R Levels

As shown in FIG. 11A-B, IL-7AT provided an attenuated signal. The levels of IL-7 receptor (IL-7R) and intracellular phospho-STAT5 were used as indicators of the potency of the IL-7 signal. The levels of surface IL-7R inversely correlated with the strength of the IL-7 signal-high dose IL-7 causes receptor down regulation, while, in the absence of the cytokine, receptor levels increases (Park et al., 2004). IL-7AT-treated D1-CD4 or D1 cells had higher levels of IL-7R, as compared to native IL-7 (at the same low dose), indicative of attenuated signaling, while viability was equivalent (FIG. 11A). Reduced intracellular phospho-STAT5 showed that signaling through IL-7R was attenuated in IL-7AT-treated cells, as compared to IL-7-treated cells at equivalent doses (FIG. 11B).

Example 10

Adjust the Strength of the IL-7 Signal to Improve Immune Reconstitution

Failure to successfully reconstitute immune cells after SCT is associated with severe infections, cancer relapse and the development of secondary malignancies. GVHD also complicates recovery. Treatment options for patients after SCT are limited to prophylactics against infectious agents. As disclosed herein, it is believed that the use of IL-7A polypeptide promotes effective immune reconstitution after SCT. Ex vivo treatment of lymphocyte progenitors in the bone marrow graft with an IL-7A polypeptide improves the subsequent reconstitution of lymphocytes. An IL-7A polypeptide was purified as described herein the activity of an IL-7A polypeptide was tested using human bone marrow stem cells. The particular IL-7A polypeptide used in this experiment has the amino acid sequence of SEQ. ID NO. 4, though other polypeptides disclosed herein can be used.

Collaborators at Florida Hospital provided six-eight human stem cell samples for treatment with an IL-7A polypeptide. The phenotype of the stem cell populations is established prior to and after culture with the IL-7A polypeptide and the viability and proliferative status of the treated cells was documented. To determine whether the IL-7A polypeptide can sustain immune reconstitution, the cytokine in murine models of autologous and allogeneic bone marrow transplantation (BMT) is tested. Donor bone marrow cells are pre-treated with the IL-7A polypeptide and then infused into lethally irradiated mice. The recovery of immune cells in lymphoid organs and potential for GVHD after 28 days post-transplant is examined. Testing of the IL-7A polypeptide in the pre-treatment of stem cells shows that an attenuated IL-7 signal can promote immune reconstitution by supporting the viability of lymphoid progenitors in stem cell population without later causing GVHD. The practical use of the IL-7A polypeptide as an agent for immune reconstitution after SCT is demonstrated, as well as using these techniques as a therapeutic approach in the ex vivo treatment of lymphoid progenitor cells found in bone marrow grafts.

Example 11

Test the Activity of IL-7 Ligand on the Growth of Human Lymphoid Progenitor Cells A therapeutic use for ligand is the pre-treatment of the lymphoid progenitor cells found stem cell grafts used to reconstitute patients undergoing SCT treatments. The current practice for recovering stem cells is to treat patients (autologous) or donors with G-CSF to cause the release of bone marrow cells into the blood (Buzzeo et al., 2007). Blood, containing peripheral blood mononuclear cells (PBMCs), bone marrow progenitor and stem cells, was collected and frozen for use The effectiveness of IL-7 ligand to treat peripheral blood stem cells and promote immune reconstitution was tested. Six-eight human peripheral blood samples were used for testing with ligand. Phenotype cells were tested prior to treatment with ligand (or IL-7) for surface expression of CD127 (IL-7R), CD3 (T-cells. The proportion of hematopoietic stems cells (HSC) (CD34$^+$) and common lymphoid progenitors (CLP) (CD34$^+$117r$^{++}$) in the population was determined. Viability and proliferation of peripheral blood stem cells in long term culture with cytokines was assessed as described. After treatments with ligand (IL-7AT polypeptide) (or IL-7), phenotype cells for surface markers described above were tested to determine if treatment with cytokines altered the immune cell subset distribution. Treatment with ligand supported the viability of multiple immune cell types and specifically enabled the survival of IL-7R+ expressing lymphoid progenitor cells that have the potential to give rise to T-cells. These findings established the use of ligand as a treatment to improve the survival of cells used in the transplantation process.

Figure 12:
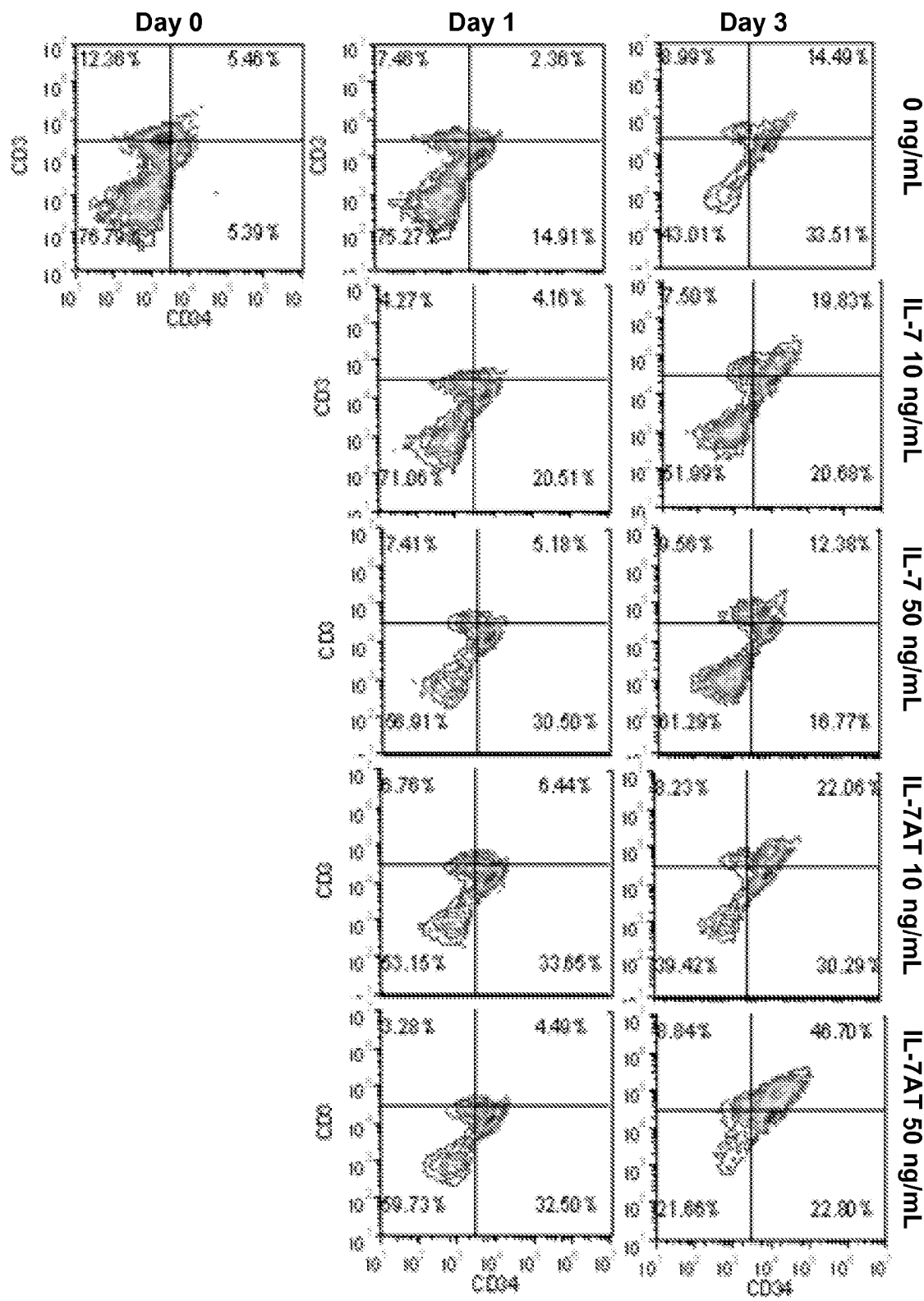
FIG. 12 show CD34 stem cell expansion and pre-T cell differentiation was supported.

As shown in FIG. 12A-C, IL-7AT supports CD34 stem cell expansion and pre-T cell differentiation. Human peripheral blood enriched with stem cells was cultured in stem cell media for 0-3 days and untreated (0) or treated with IL-7AT or IL-7 at low dose (10 ng/ml) or high dose (50 ng/ml). Cells were phenotyped by flow cytometry using antibodies to detect CD34 or CD3. Gating was determined using control antibodies. Treatment with IL-7AT after 3 days led to the expansion of a predominant CD34 population and the emergence of new population of CD34, CD3 cells.

Figure 13:
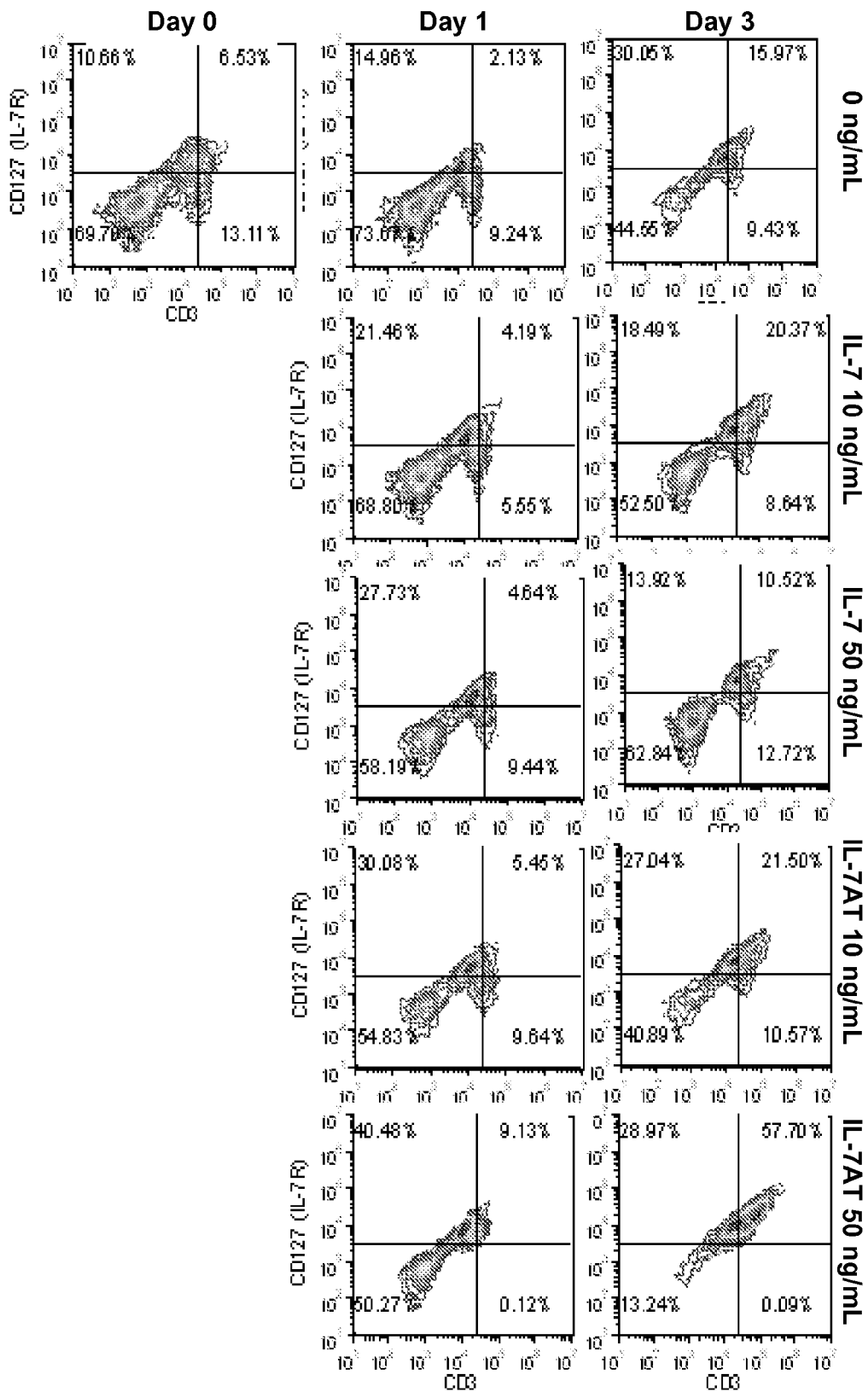
FIG. 13 show IL-7R levels were maintained on CD3+ cells.

As shown in FIG. 13A-C, IL-7AT maintained IL-7R levels on CD3+ cells. Human peripheral blood enriched with stem cells was cultured in stem cell media for 0-3 days and untreated (0) or treated with IL-7AT or IL-7 at low dose (10 ng/ml) or high dose (50 ng/ml). Cells were phenotyped by flow cytometry using antibodies to detect CD127 (IL-7R) and CD3. Gating was determined using control antibodies. Treatment with IL-7AT after 3 days led to the expansion of CD3 cells that maintained high levels of the IL-7R.

Figure 14:
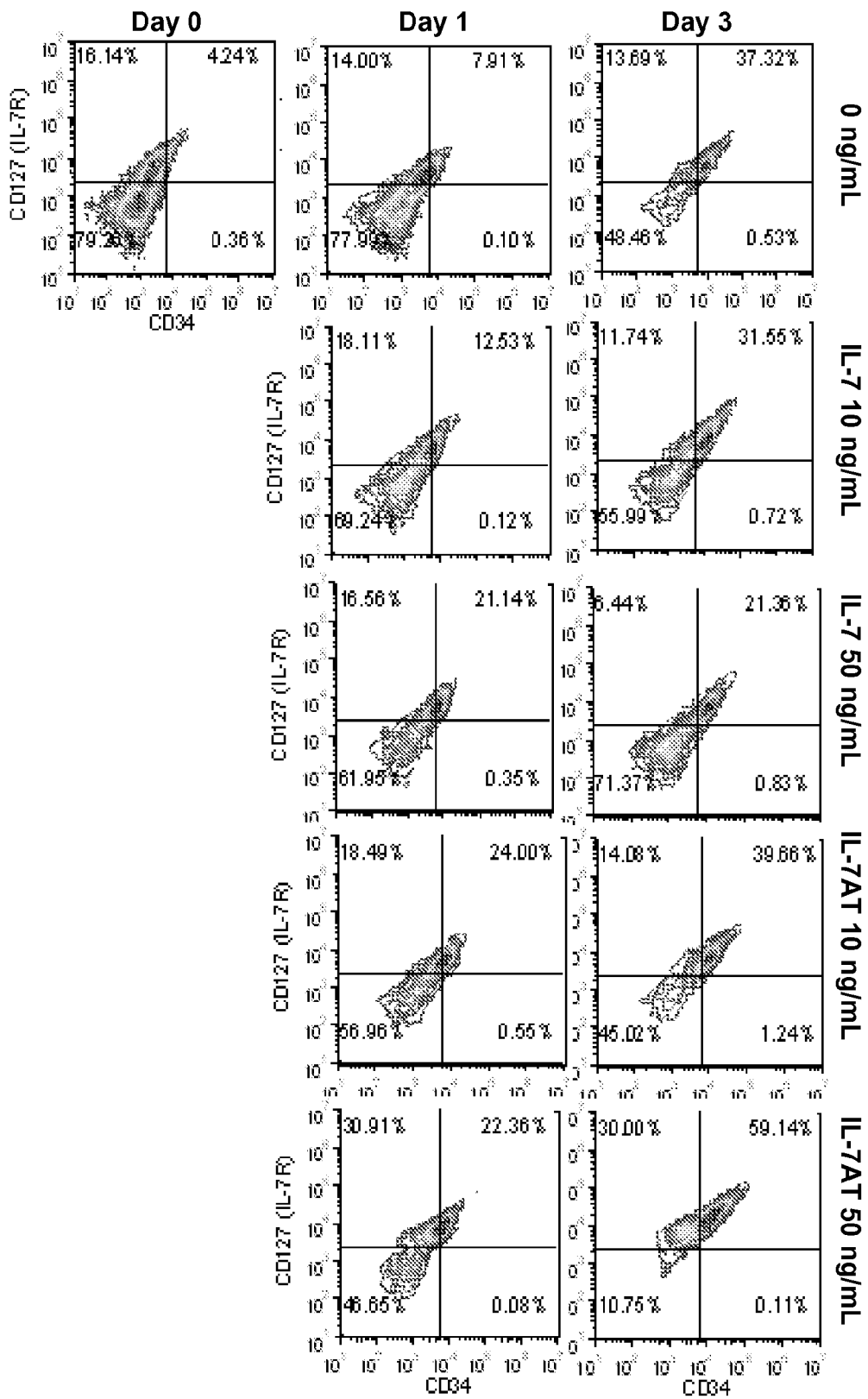
FIG. 14 show IL-7R levels were maintained on CD34+ cells.

As shown in FIG. 14A-C, IL-7AT maintained IL-7R levels on CD34+ cells. Human peripheral blood enriched with stem cells was cultured in stem cell media for 0-3 days and untreated (0) or treated with IL-7AT or IL-7 at low dose (10 ng/ml) or high dose (50 ng/ml). Cells were phenotyped by flow cytometry using antibodies to detect CD127 (IL-7R) and CD34. Gating was determined using control antibodies. Treatment with IL-7AT after 3 days led to the expansion of CD34 cells that maintained high levels of the IL-7R.

Example 12

Examine the Effect of Conditioning Bone Marrow Cells With IL-7 Ligand in Murine Models of BMT To determine whether IL-7 ligand can support immune reconstitution, the attenuated cytokine in murine models of autologous or allogeneic BMT is tested. Donor bone marrow cells are recovered from the femurs and tibias of C57B1/6 or Balb/c mice and are pre-treated with ligand (or IL-7 as control) for the optimal time and dose as determined in Example 7, 1.3 and Example 8, 2.2. The phenotype of the bone marrow cells as described in 2.2 is determined to track the IL-7R$^+$ cells and the HSC and CLP populations before and after treatment with ligand (or IL-7) is identified. On day 0, the recipient C57B1/6 mice are lethally irradiated, receiving 1300 cGy of total body irradiation. Irradiated mice are given an infusion of 5-10×10$^6$ untreated, IL-7-treated or ligand-treated C57B1/6 or Balb/c bone marrow cells by tail vein injection. From day 15-28, mice receive BrdU (0.8 mg/ml) in their drinking water. During the reconstitution period mice are weighed and monitored for signs indicative of GVHD.

After 4 weeks (28 days) mice are sacrificed and lymphoid organs recovered for analysis. The proliferation of spleen and lymph node T-cells by measuring BrdU uptake by flow cytometry using specific antibodies (BrdU Flow Kit, BD Biosciences) is assessed. The phenotype of spleen and lymph node cells for surface markers is assessed to determine distribution of T cells, B cells, myeloid cells and NK cells as described. Splenic and lymph node CD3+ T cells are isolated, phenotyped for naïve and memory markers (CD44, CD62L), and stimulated with anti-CD3 and anti-CD28 to mimic TCR signaling and measure levels of LCK and Zap-70. Additionally, cytokine production, specifically IL-2, IFN-γ and IL-4 is assessed to determine effector status and measure BCL-2 levels and correlate to phospho-STAT5 levels to evaluate survival signaling. Histological examination of lymphocyte infiltration in organs from mice that die prematurely is performed. Four separate BMT experiments are conducted with each experiment using nine recipient mice. IL-7 ligand can effectively promote immune reconstitution after BMT without provoking GVHD. Pre-treatment with ligand expanded the lymphoid progenitor cells in the bone marrow graft to allow rapid engraftment and reconstitution after transplant. As evidence of this, increased BrdU+ T-cells from lymphoid organs are detected, as compared to the untreated or IL-7-treated bone marrow transplant. Specifically, T-cells are activated by TCR signaling and produced effector molecules (IL-4) indicative that ligand reconstituted a fully functional immune system.

Methods and compositions of the present invention comprising IL-7AT polypeptides provide an ex vivo treatment of lymphocyte progenitors in bone marrow for transplant into patients undergoing SCT for cancer therapy. The invention comprises an efficient method for large scale production of ligand that is commercially adapted to produce the cytokine. Treatment of human lymphoid progenitor cells with IL-7A resulted in increased viability, indicating that this treatment improves the reconstitution potential of the transplant. It is shown that treatment of bone marrow cells with IL-7A improved the immune reconstitution of lethally irradiated mice receiving BMT and, in the allogeneic model, minimize GVHD. These results suggest the use of IL-7A polypeptide in patients undergoing SCT to improve outcomes by restoring immune competency and preventing cancer growth.

REFERENCE LIST

Alpdogan, O., Muriglan, S. J., Eng, J. M., Willis, L. M., Greenberg, A. S., Kappel, B. J., and van den Brink, M. R. (2003). IL-7 enhances peripheral T cell reconstitution after allogeneic hematopoietic stem cell transplantation. J. Clin. Invest 112, 1095-1107.

Alpdogan, O., Schmaltz, C., Muriglan, S. J., Kappel, B. J., Perales, M. A., Rotolo, J. A., Halm, J. A., Rich, B. E., and van den Brink, M. R. (2001). Administration of interleukin-7 after allogeneic bone marrow transplantation improves immune reconstitution without aggravating graft-versus-host disease. Blood 98, 2256-2265.

Awong, G., Herer, E., Surh, C. D., Dick, J. E., La Motte-Mohs, R. N., and Zuniga-Pflucker, J. C. (2009). Characterization in vitro and engraftment potential in vivo of human progenitor T cells generated from hematopoietic stem cells. Blood 114, 972-982.

Beq, S., Rozlan, S., Gautier, D., Parker, R., Mersseman, V., Schilte, C., Assouline, B., Rance, I., Lavedan, P., Morre, M., and Cheynier, R. (2009). Injection of glycosylated recombinant simian IL-7 provokes rapid and massive T-cell homing in rhesus macaques. Blood 114, 816-825.

Buzzeo, M. P., Yang, J., Casella, G., and Reddy, V. (2007). Hematopoietic stem cell mobilization with G-CSF induces innate inflammation yet suppresses adaptive immune gene expression as revealed by microarray analysis. Exp. Hematol. 35, 1456-1465.

Chehtane, M. and Khaled, A. R. (2010). Interleukin-7 Mediates Glucose Utilization in Lymphocytes through Transcriptional Regulation of the Hexokinase 11 Gene. Am. J. Physiol Cell Physiol.

Chung, B., DudI, E., Toyama, A., Barsky, L., and Weinberg, K. I. (2008). Importance of interleukin-7 in the development of experimental graft-versus-host disease. Biol. Blood Marrow Transplant. 14, 16-27.

Chung, B., DudI, E. P., Min, D., Barsky, L., Smiley, N., and Weinberg, K. I. (2007). Prevention of graft-versus-host disease by anti IL-7 Ralpha antibody. Blood 110, 2803-2810.

de, W. T., Suciu, S., Brand, R., Muus, P., and Kroger, N. (2007). Autologous stem cell transplantation in myelodysplastic syndromes. Semin. Hematol. 44, 274-277.

Fry, T. J., Connick, E., Falloon, J., Lederman, M. M., Liewehr, D. J., Spritzler, J., Steinberg, S. M., Wood, L. V., Yarchoan, R., Zuckerman, J., Landay, A., and Mackall, C. L. (2001). A potential role for interleukin-7 in T-cell homeostasis. Blood 97, 2983-2990.

Khaled, A. R., Bulavin, D. V., Kittipatarin, C., Li, W. Q., Alvarez, M., Kim, K., Young, H. A., Fornace, A. J., and Durum, S. K. (2005). Cytokine-driven cell cycling is mediated through Cdc25A. J. Cell Biol. 169, 755-763.

Kieper, W. C., Tan, J. T., Bondi-Boyd, B., Gapin, L., Sprent, J., Ceredig, R., and Surh, C. D. (2002). Overexpression of Interleukin (IL)-7 Leads to IL-15-independent Generation of Memory Phenotype CD8(+) T Cells. J Exp Med 195, 1533-1539.

Kim, K., Khaled, A. R., Reynolds, D., Young, H. A., Lee, C. K., and Durum, S. K. (2003). Characterization of an interleukin-7-dependent thymic cell line derived from a p53 (−/−) mouse. J. Immunol. Methods 274, 177-184.

Kittipatarin, C. and Khaled, A. R. (2007). Interlinking interleukin-7. Cytokine 39, 75-83.

Kittipatarin, C. and Khaled, A. R. (2009). Ex vivo expansion of memory CD8 T cells from lymph nodes or spleen through in vitro culture with interleukin-7. J. Immunol. Methods 344, 45-57.

Kittipatarin, C., Li, W., Durum, S. K., and Khaled, A. R. (2010a). Cdc25A-Driven Proliferation Regulates Lymphocyte Movement in Response to Interleukin-7. Exp. Hematol. 38, 1143-1156.

Kittipatarin, C., Tschammer, N., and Khaled, A. R. (2010b). The interaction of LCK and the CD4 co-receptor alters the dose response of T-cells to interleukin-7. Immunol. Lett. 131, 170-181.

Kovanen, P. E. and Leonard, W. J. (2004). Cytokines and immunodeficiency diseases: critical roles of the gamma (c)-dependent cytokines interleukins 2, 4, 7, 9, 15, and 21, and their signaling pathways. Immunol. Rev. 202, 67-83.

Link, A., Vogt, T. K., Favre, S., Britschgi, M. R., cha-Orbea, H., Hinz, B., Cyster, J. G., and Luther, S. A. (2007). Fibroblastic reticular cells in lymph nodes regulate the homeostasis of naive T cells. Nat. Immunol. 8, 1255-1265.

Namen, A. E., Schmierer, A. E., March, C. J., Overell, R. W., Park, L. S., Urdal, D. L., and Mochizuki, D. Y. (1988). B cell precursor growth-promoting activity. Purification and characterization of a growth factor active on lymphocyte precursors. J Exp Med 167, 988-1002.

Park, J. H., Yu, Q., Erman, B., Appelbaum, J. S., Montoya-Durango, D., Grimes, H. L., and Singer, A. (2004). Suppression of IL-7 Ralpha transcription by IL-7 and other prosurvival cytokines: a novel mechanism for maximizing IL-7-dependent T cell survival. Immunity. 21, 289-302.

Rich, B. E., Campos-Torres, J., Tepper, R. I., Moreadith, R. W., and Leder, P. (1993). Cutaneous lymphoproliferation and lymphomas in interleukin 7 transgenic mice. J Exp Med 177, 305-316.

Sakata, T., Iwagami, S., Tsuruta, Y., Teraoka, H., Tatsumi, Y., Kita, Y., Nishikawa, S., Takai, Y., and Fujiwara, H. (1990). Constitutive expression of interleukin-7 mRNA and production of IL-7 by a cloned murine thymic stromal cell line. J. Leukoc. Biol. 48, 205-212.

Sawa, Y., Arima, Y., Ogura, H., Kitabayashi, C., Jiang, J. J., Fukushima, T., Kamimura, D., Hirano, T., and Murakami, M. (2009). Hepatic interleukin-7 expression regulates T cell responses. Immunity. 30, 447-457.

Schluns, K. S., Kieper, W. C., Jameson, S. C., and Lefrancois, L. (2000). Interleukin-7 mediates the homeostasis of naive and memory CD8 T cells in vivo. Nat Immunol 1, 426-432.

Shalapour, S., Deiser, K., Sercan, O., Tuckermann, J., Minnich, K., Willimsky, G., Blankenstein, T., Hammerling, G. J., Arnold, B., and Schuler, T. (2010). Commensal microflora and interferon-gamma promote steady-state interleukin-7 production in vivo. Eur. J. Immunol. 40, 2391-2400.

Shultz, L. D., Lyons, B. L., Burzenski, L. M., Gott, B., Chen, X., Chaleff, S., Kotb, M., Gillies, S. D., King, M., Mangada, J., Greiner, D. L., and Handgretinger, R. (2005). Human lymphoid and myeloid cell development in NOD/LtSz-scid IL2R gamma null mice engrafted with mobilized human hemopoietic stem cells. J. Immunol. 174, 6477-6489.

Smith, K. A. (2001). Low-dose daily interleukin-2 immunotherapy: accelerating immune restoration and expanding HIV-specific T-cell immunity without toxicity. AIDS 15 Suppl 2, S28-S35.

Sportes, C., Babb, R. R., Krumlauf, M. C., Hakim, F. T., Steinberg, S. M., Chow, C. K., Brown, M. R., Fleisher, T. A., Noel, P., Maric, I., Stetler-Stevenson, M., Engel, J., Buffet, R., Morre, M., Amato, R. J., Pecora, A., Mackall, C. L., and Gress, R. E. (2010). Phase I study of recombinant human interleukin-7 administration in subjects with refractory malignancy. Clin. Cancer Res. 16, 727-735.

Sportes, C., Hakim, F. T., Memon, S. A., Zhang, H., Chua, K. S., Brown, M. R., Fleisher, T. A., Krumlauf, M. C., Babb, R. R., Chow, C. K., Fry, T. J., Engels, J., Buffet, R., Morre, M., Amato, R. J., Venzon, D. J., Korngold, R., Pecora, A., Gress, R. E., and Mackall, C. L. (2008). Administration of rhIL-7 in humans increases in vivo TCR repertoire diversity by preferential expansion of naive T cell subsets. J. Exp. Med. 205, 1701-1714.

Tallman, M. S. (2007). Treatment of relapsed or refractory acute promyelocytic leukemia. Best. Pract. Res. Clin. Haematol. 20, 57-65.

Thiant, S., Yakoub-Agha, I., Magro, L., Trauet, J., Coiteux, V., Jouet, J. P., Dessaint, J. P., and Labalette, M. (2010). Plasma levels of IL-7 and IL-15 in the first month after myeloablative BMT are predictive biomarkers of both acute GVHD and relapse. Bone Marrow Transplant. 45, 1546-1552.

Vigouroux, S., Michallet, M., Porcher, R., Attal, M., Ades, L., Bernard, M., Blaise, D., Tabrizi, R., Garban, F., Cassuto, J. P., Chevalier, P., Facon, T., Ifrah, N., Renaud, M., Tilly, H., Vernant, J. P., Kuentz, M., Bourhis, J. H., Bordigoni, P., Deconinck, E., Lioure, B., Socie, G., and Milpied, N. (2007). Long-term outcomes after reduced-intensity conditioning allogeneic stem cell transplantation for low-grade lymphoma: a survey by the French Society of Bone Marrow Graft Transplantation and Cellular Therapy (SFGM-TC). Haematologica 92, 627-634.

von-Freeden-Jeffry, U., Vieira, P., Lucian, L. A., McNeil, T., Burdach, S. E., and Murray, R. (1995). Lymphopenia in interleukin (IL)-7 gene-deleted mice identifies IL-7 as a non-redundant cytokine. J Exp Med 181, 1519-1526.

Warlick, E. D., O'Donnell, P. V., Borowitz, M., Grupka, N., Decloe, L., Garrett-Mayer, E., Borrello, I., Brodsky, R., Fuchs, E., Huff, C. A., Luznik, L., Matsui, W., Ambinder, R., Jones, R. J., and Douglas, S. B. (2008). Myeloablative allogeneic bone marrow transplant using T cell depleted allografts followed by post-transplant GM-CSF in high-risk myelodysplastic syndromes. Leuk. Res. 32, 1439-1447.

Yamanaka, K., Clark, R., Rich, B., Dowgiert, R., Hirahara, K., Hurwitz, D., Shibata, M., Mirchandani, N., Jones, D. A., Goddard, D. S., Eapen, S., Mizutani, H., and Kupper, T. S. (2006). Skin-derived interleukin-7 contributes to the proliferation of lymphocytes in cutaneous T-cell lymphoma. Blood 107, 2440-2445.

What is claimed is:

1. An isolated IL-7 mutant protein, derived from a wild type IL-7 protein having the amino acid sequence as set forth in SEQ ID NO:7, having an amino acid substitution at site T97, wherein the IL-7 mutant protein has reduced binding to an IL-7 receptor compared to binding of the wild type IL-7 protein to the IL-7 receptor.

2. The IL-7 mutant protein of claim 1, wherein the binding of the IL-7 mutant protein to the IL-7 receptor causes an attenuated signal by the receptor.

3. The IL-7 mutant protein of claim 1, wherein the T97 is substituted with valine.

4. A composition comprising the IL-7 mutant protein of claim 1.

5. The composition of claim 4, wherein the T97 of the IL-7 mutant protein is substituted with valine.

6. The composition of claim 4, further comprising a pharmaceutically acceptable carrier.

7. An isolated nucleic acid encoding an IL-7 mutant protein derived from a wild type of IL-7 protein having the amino acid sequence as set forth in SEQ ID NO:7, having an amino acid substitution at site T97, wherein the IL-7 mutant protein has reduced binding to an IL-7 receptor compared to binding of the wild type IL-7 protein to the IL-7 receptor.

8. The isolated nucleic acid of claim 7, comprising the nucleotide sequence of SEQ ID NO:3.

9. A vector comprising the nucleic acid of claim 7 or claim 8.

10. An isolated host cell comprising the nucleic acid of claim 7 or claim 8.

* * * * *